(12) United States Patent
Haviv et al.

(10) Patent No.: US 7,169,888 B2
(45) Date of Patent: Jan. 30, 2007

(54) TETRA-, PENTA-, HEXA- AND HEPTAPEPTIDES HAVING ANTIANGIOGENIC ACTIVITY

(75) Inventors: Fortuna Haviv, Deerfield, IL (US); Michael F. Bradley, Wadsworth, IL (US)

(73) Assignee: Abbott Laboratories, Abbott Park, IL (US)

( * ) Notice: Subject to any disclaimer, the term of this patent is extended or adjusted under 35 U.S.C. 154(b) by 552 days.

(21) Appl. No.: 10/283,549

(22) Filed: Oct. 30, 2002

(65) Prior Publication Data

US 2003/0105023 A1    Jun. 5, 2003

Related U.S. Application Data

(60) Provisional application No. 60/335,019, filed on Oct. 31, 2001, provisional application No. 60/335,412, filed on Oct. 31, 2001.

(51) Int. Cl.
*A61K 38/03* (2006.01)
(52) U.S. Cl. .................................... 530/300
(58) Field of Classification Search ................ 514/16, 514/17; 530/328, 329
See application file for complete search history.

(56) References Cited

U.S. PATENT DOCUMENTS 5,140,009 A * 8/1992 Haviv et al. .................. 514/16

FOREIGN PATENT DOCUMENTS

| WO | 99/61476 | 12/1999 |
|---|---|---|
| WO | 01/38347 | 5/2001 |
| WO | 01/38397 | 5/2001 |

OTHER PUBLICATIONS

Flouret, et al., Effects of D-Amino Acid Substituents on Degradation of LHRH Analogues by Proximal Tubule, American Journal of Physiology, Mar. 1987, vol. 272, Issue 3, Pt. 1, pp. E320-326.*
Bagley, et al., Endothelial Precursor Cells As a Model of Tumor Endothelium : Characterization and Comparison with Mature Endothelial Cells, Cancer Research, Sep. 15, 2003, vol. 63, pp. 5866-5873.*
Harvey Black, Angiogenesis—Promoting and Blocking—Comes into Focus, The Scientist, Apr. 27, 1998, vol. 12, No. 9, pp. 10-14.*
Scott Veggeberg, Fighting Cancer with Angiogenesis Inhibitors, The Scientist, May 27, 2002, vol. 16, No. 11, pp. 41-46.*
Trisha Gura, Systems for Identifying New Drugs are Often Faulty, Science, Nov. 7, 1997, vol. 278, pp. 1041-1042.*
Gerald B. Dermer, Another Anniversary for the War on Cancer, Biotechnology, Mar. 1994, vol. 12, p. 320.*
Flouret et al. "Effects of D-amino acid substituents on degradation of LHRH analogoues by proximal tubule." Am. J. Physiol. 1987, 252, E320-E326.*
Yang et al. "Characterization of proteolytic activites of pulmonary alveolar epithelium." Int. J. Pharm. 2000, 195, 93-101.*
Hagedom & Bikfalvi "Target molecules for anti-angiogenic therapy: from basic research to clinical trials." Crit. Rev. Onc./Hemat., 2000, 34, 89-110.*

* cited by examiner

*Primary Examiner*—Cecilia J. Tsang
*Assistant Examiner*—Christina M. Bradley
(74) *Attorney, Agent, or Firm*—Johanna M. Corbin; Gregory W Steele

(57) ABSTRACT

Compounds of formula (SEQ ID NO:2) and (SEQ ID NO:3), which are useful for treating conditions that arise from or are exacerbated by angiogenesis, are described. Also disclosed are pharmaceutical compositions comprising these compounds, methods of treatment using these compounds, and methods of inhibiting angiogenesis.

12 Claims, No Drawings

TETRA-, PENTA-, HEXA- AND HEPTAPEPTIDES HAVING ANTIANGIOGENIC ACTIVITY

CROSS-REFERENCE TO RELATED APPLICATIONS

This application claims priority to U.S. Provisional Patent Application Ser. No. 60/335,019, filed on Oct. 31, 2001, and U.S. Provisional Patent Application Ser. No. 60/335,412, filed on Oct. 31, 2001, which are both hereby incorporated by reference.

TECHNICAL FIELD

The present invention relates to methods of inhibiting angiogenesis, methods of treating cancer, and compounds having activity useful for treating conditions which arise from or are exacerbated by angiogenesis. Also disclosed are pharmaceutical compositions comprising the compounds and methods of treatment using the compounds.

BACKGROUND OF THE INVENTION

Angiogenesis is the fundamental process by which new blood vessels are formed and is essential to a variety of normal body activities (such as reproduction, development and wound repair). Although the process is not completely understood, it is believed to involve a complex interplay of molecules which both stimulate and inhibit the growth of endothelial cells, the primary cells of the capillary blood vessels. Under normal conditions these molecules appear to maintain the microvasculature in a quiescent state (i.e., one of no capillary growth) for prolonged periods that may last for weeks, or in some cases, decades. However, when necessary, such as during wound repair, these same cells can undergo rapid proliferation and turnover within as little as five days.

Although angiogenesis is a highly regulated process under normal conditions, many diseases (characterized as "angiogenic diseases") are driven by persistent unregulated angiogenesis. Otherwise stated, unregulated angiogenesis may either cause a particular disease directly or exacerbate an existing pathological condition. For example, the growth and metastasis of solid tumors have been shown to be angiogenesis-dependent. Based on these findings, there is a continuing need for compounds which demonstrate antiangiogenic activity due to their potential use in the treatment of various diseases such as cancer.

Peptides having angiogenesis inhibiting properties have been described in commonly-owned WO01/38397, WO01/38347, WO99/61476, and U.S. patent application Ser. No. 09/915,956. However, it would be desirable to prepare antiangiogenic compounds having improved profiles of activity and smaller size.

SUMMARY OF THE INVENTION

The present invention relates to a novel class of compounds having angiogenesis-inhibiting properties. The invention provides tetra-, penta-, hexa-, and heptapeptides with enhanced properties of angiogenesis inhibition. In its principle embodiment, the present invention provides a compound of formula (I)

$Xaa_1$-$Xaa_2$-$Xaa_3$-$Xaa_4$-$Xaa_5$-$Xaa_6$-$Xaa_7$-$Xaa_8$    (I),(SEQ ID NO:1)

or a therapeutically acceptable salt thereof, wherein $Xaa_1$ is selected from the group consisting of hydrogen and R—$(CH_2)_n$—C(O)—, wherein n is an integer from 0 to 8 and R is selected from the group consisting of alkoxy, alkyl, amino, aryl, carboxyl, cycloalkenyl, cycloalkyl, and heterocycle;

$Xaa_2$ is absent or selected from the group consisting of β-alanyl, D-alanyl, D-alloisoleucyl, D-allylglycyl, D-4-chlorophenylalanyl, D-citrullyl, D-3-cyanophenylalanyl, D-homophenylalanyl, D-homoseryl, isoleucyl, D-isoleucyl, D-leucyl, N-methyl-D-leucyl, D-norleucyl, D-norvalyl, D-penicillaminyl, D-phenylalanyl, D-prolyl, D-seryl, D-thienylalanyl, and D-threonyl;

$Xaa_3$ is selected from the group consisting of D-alanyl, D-alloisoleucyl, allothreonyl, allylglycyl, asparaginyl, aspartyl, glutaminyl, D-glutaminyl, N-methylglutaminyl, glutamyl, N-methylglutamyl, glycyl, histidyl, homoseryl, D-homoseryl, isoleucyl, D-isoleucyl, lysyl(N-epsilon-acetyl), methionyl, D-methionyl, norleucyl, D-norleucyl, norvalyl, D-norvalyl, D-prolyl, sarcosyl, seryl, D-seryl, N-methylseryl, threonyl, D-threonyl, tryptyl, tyrosyl, and tyrosyl(O-methyl);

$Xaa_4$ is selected from the group consisting of N-methylalanyl, allothreonyl, arginyl, asparaginyl, D-asparaginyl, citrullyl, glutaminyl, D-glutaminyl, glutamyl, glycyl, homoseryl, leucyl, D-leucyl, lysyl(N-epsilon-acetyl), lysyl(N-epsilon-nicotinyl), norleucyl, norvalyl, D-norvalyl, N-methylnorvalyl, ornithyl(N-delta-acetyl), 3-(3-pyridyl)alanyl, sarcosyl, seryl, D-seryl, N-methylseryl, threonyl, tryptyl, valyl, and N-methylvalyl;

$Xaa_5$ is selected from the group consisting of alanyl, alloisoleucyl, aspartyl, citrullyl, glutaminyl, isoleucyl, D-isoleucyl, N-methylisoleucyl, leucyl, D-leucyl, lysyl, lysyl(N-epsilon-acetyl), D-lysyl(N-epsilon-acetyl), norleucyl, norvalyl, phenylalanyl, prolyl, D-prolyl, and valyl;

$Xaa_6$ is selected from the group consisting of D-alloisoleucyl, arginyl, D-arginyl, citrullyl, histidyl, lysyl, lysyl(N-epsilon-isopropyl), ornithyl, and 3-(3-pyridyl)alanyl;

$Xaa_7$ is absent or selected from the group consisting of N-methyl-D-alanyl, 2-aminobutyryl, 2-aminoisobutyryl, D-glutaminyl, homoprolyl, hydroxyprolyl, leucyl, phenylalanyl, prolyl, D-prolyl, threonyl, and D-valyl; and $Xaa_8$ is selected from the group consisting of D-alanylamide, azaglycylamide, glycylamide, hydroxyl, D-lysyl(N-epsilon-acetyl)amide, a group represented by the formula —NH—$(CH_2)_n$—$CHR^1R^2$; and a group represented by the formula —$NHR^3$, wherein n is an integer from 0 to 8; $R^1$ is selected from the group consisting of hydrogen, alkyl, cycloalkenyl, and cycloalkyl; $R^2$ is selected from the group consisting of hydrogen, alkoxy, alkyl, aryl, cycloalkenyl, cycloalkyl, heterocycle, and hydroxyl, provided that when n is 0, $R^2$ is other than alkoxy or hydroxyl; and $R^3$ is selected from the group consisting of hydrogen, cycloalkenyl, cycloalkyl, and hydroxyl; and provided that when $Xaa_6$ is D-alloisoleucyl, $Xaa_7$ is threonyl and $Xaa_8$ is hydroxyl.

In a preferred embodiment, the present invention provides a compound of formula (II)

$Xaa_1$-$Xaa_2$-$Xaa_3$-$Xaa_4$-$Xaa_5$-$Xaa_6$-$Xaa_7$-$Xaa_8$    (II),(SEQ ID NO:2)

or a therapeutically acceptable salt thereof, wherein $Xaa_1$ is absent or R—$(CH_2)_n$—C(O)—, wherein n is an integer from 0 to 8 and R is selected from the group consisting of alkoxy, alkyl, amino, aryl, carboxyl, cycloalkenyl, cycloalkyl, and heterocycle;

$Xaa_2$ is selected from the group consisting of β-alanyl, D-alanyl, D-alloisoleucyl, D-allylglycyl, D-4-chlorophenylalanyl, D-citrullyl, D-3-cyanophenylalanyl, D-homophenylalanyl, D-homoseryl, isoleucyl, D-isoleucyl, D-leucyl, N-methyl-D-leucyl, D-norleucyl, D-norvalyl, D-penicillaminyl, D-phenylalanyl, D-prolyl, D-seryl, D-thienylalanyl, and D-threonyl;

$Xaa_3$ is selected from the group consisting of allothreonyl, aspartyl, glutaminyl, D-glutaminyl, N-methylglutaminyl, glycyl, histidyl, homoseryl, isoleucyl, lysyl(N-epsilon-acetyl), methionyl, seryl, N-methylseryl, threonyl, D-threonyl, tryptyl, tyrosyl, and tyrosyl(O-methyl);

$Xaa_4$ is selected from the group consisting of N-methylalanyl, allothreonyl, arginyl, glutaminyl, D-glutaminyl, glycyl, homoseryl, leucyl, lysyl(N-epsilon-acetyl), norleucyl, norvalyl, D-norvalyl, N-methylnorvalyl, ornithyl(N-delta-acetyl), 3-(3-pyridyl)alanyl, sarcosyl, seryl, N-methylseryl, threonyl, tryptyl, valyl and N-methylvalyl;

$Xaa_5$ is selected from the group consisting of alanyl, alloisoleucyl, aspartyl, citrullyl, glutaminyl, isoleucyl, D-isoleucyl, N-methylisoleucyl, leucyl, D-leucyl, lysyl, lysyl(N-epsilon-acetyl), D-lysyl(N-epsilon-acetyl), norleucyl, norvalyl, phenylalanyl, prolyl, and D-prolyl;

$Xaa_6$ is selected from the group consisting of arginyl, D-arginyl, citrullyl, histidyl, lysyl, lysyl(N-epsilon-isopropyl), ornithyl, and 3-(3-pyridyl)alanyl;

$Xaa_7$ is absent or selected from the group consisting of N-methyl-D-alanyl, 2-aminobutyryl, 2-aminoisobutyryl, D-glutaminyl, homoprolyl, hydroxyprolyl, leucyl, phenylalanyl, prolyl, D-prolyl, and D-valyl; and $Xaa_8$ is selected from the group consisting of D-alanylamide, azaglycylamide, glycylamide, hydroxyl, D-lysyl(N-epsilon-acetyl)amide, a group represented by the formula —NH—$(CH_2)_n$—$CHR^1R^2$; and a group represented by the formula —$NHR^3$, wherein n is an integer from 0 to 8; $R^1$ is selected from the group consisting of hydrogen, alkyl, cycloalkenyl, and cycloalkyl; $R^2$ is selected from the group consisting of hydrogen, alkoxy, alkyl, aryl, cycloalkenyl, cycloalkyl, heterocycle, and hydroxyl, with the proviso that when n is 0, $R^2$ is other than alkoxy or hydroxyl; and $R^3$ is selected from the group consisting of hydrogen, cycloalkenyl, cycloalkyl, and hydroxyl.

In a more preferred embodiment, the present invention provides a compound of formula (II), or a therapeutically acceptable salt thereof, wherein $Xaa_2$ is selected from the group consisting of β-alanyl, D-alloisoleucyl, D-4-chlorophenylalanyl, D-homophenylalanyl, D-leucyl, D-penicillaminyl, and D-prolyl; and $Xaa_1$, $Xaa_3$, $Xaa_4$, $Xaa_5$, $Xaa_6$, $Xaa_7$, and $Xaa_8$ are as described for formula (II).

In another more preferred embodiment, the present invention provides a compound of formula (II), or a therapeutically acceptable salt thereof, wherein $Xaa_2$ is D-isoleucyl, $Xaa_3$ is selected from the group consisting of allothreonyl, aspartyl, glutaminyl, lysyl(N-epsilon-acetyl), methionyl, seryl, and tyrosyl, and $Xaa_1$, $Xaa_4$, $Xaa_5$, $Xaa_6$, $Xaa_7$, and $Xaa_8$ are as described for formula (II).

In another more preferred embodiment, the present invention provides a compound of formula (II), or a therapeutically acceptable salt thereof, wherein $Xaa_2$ is D-isoleucyl, $Xaa_3$ is threonyl, $Xaa_4$ is selected from the group consisting of arginyl, glutaminyl, D-glutaminyl, norleucyl, norvalyl, N-methylnorvalyl, seryl, and tryptyl, and $Xaa_1$, $Xaa_5$, $Xaa_6$, $Xaa_7$, and $Xaa_8$ are as described for formula (II).

In another embodiment, the present invention provides a pharmaceutical composition comprising a compound of formula (II), or a therapeutically acceptable salt thereof, in combination with a therapeutically acceptable carrier.

In another embodiment, the present invention provides a method of inhibiting angiogenesis in a mammal in recognized need of such treatment comprising administering to the mammal a therapeutically acceptable amount of a compound of formula (II) or a therapeutically acceptable salt thereof.

In another embodiment, the present invention provides a method of treating cancer in a mammal in recognized need of such treatment comprising administering to the mammal a therapeutically acceptable amount of a compound of formula (II) or a therapeutically acceptable salt thereof.

In another preferred embodiment, the present invention provides a compound of formula (III)

$Xaa_1$-$Xaa_2$-$Xaa_3$-$Xaa_4$-$Xaa_5$-$Xaa_6$-$Xaa_7$  (III),(SEQ ID NO:3)

or a therapeutically acceptable salt thereof, wherein $Xaa_1$ is absent or R—$(CH_2)_n$—C(O)—, wherein n is an integer from 0 to 8 and R is selected from the group consisting of alkoxy, alkyl, amino, aryl, carboxyl, cycloalkenyl, cycloalkyl, and heterocycle;

$Xaa_2$ is selected from the group consisting of D-alanyl, D-alloisoleucyl, allothreonyl, allylglycyl, asparaginyl, aspartyl, glutaminyl, D-glutaminyl, glutamyl, N-methylglutamyl, glycyl, histidyl, homoseryl, D-homoseryl, isoleucyl, D-isoleucyl, lysyl(N-epsilon-acetyl), methionyl, D-methionyl, norleucyl, D-norleucyl, norvalyl, D-norvalyl, D-prolyl, sarcosyl, seryl, D-seryl, N-methylseryl, threonyl, D-threonyl, tryptyl, tyrosyl, and tyrosyl(O-methyl);

$Xaa_3$ is selected from the group consisting of N-methylalanyl, allothreonyl, arginyl, asparaginyl, D-asparaginyl, citrullyl, glutaminyl, D-glutaminyl, glutamyl, glycyl, homoseryl, leucyl, D-leucyl, lysyl(N-epsilon-acetyl), lysyl (N-epsilon-nicotinyl), norleucyl, norvalyl, D-norvalyl, N-methylnorvalyl, ornithyl(N-delta-acetyl), 3-(3-pyridyl)alanyl, sarcosyl, seryl, D-seryl, N-methylseryl, threonyl, tryptyl, valyl, and N-methylvalyl;

$Xaa_4$ is selected from the group consisting of alanyl, alloisoleucyl, aspartyl, citrullyl, isoleucyl, D-isoleucyl, N-methylisoleucyl, leucyl, D-leucyl, lysyl, lysyl(N-epsilon-acetyl), D-lysyl(N-epsilon-acetyl), norvalyl, phenylalanyl, prolyl, D-prolyl, and valyl;

$Xaa_5$ is selected from the group consisting of D-alloisoleucyl, arginyl, D-arginyl, citrullyl, histidyl, lysyl, lysyl(N-epsilon-isopropyl), ornithyl, and 3-(3-pyridyl)alanyl;

$Xaa_6$ is absent or selected from the group consisting of N-methyl-D-alanyl, 2-aminobutyryl, 2-aminoisobutyryl, D-glutaminyl, homoprolyl, hydroxyprolyl, leucyl, phenylalanyl, prolyl, D-prolyl, threonyl, and D-valyl; and $Xaa_7$ is selected from the group consisting of D-alanylamide, azaglycylamide, glycylamide, hydroxyl, D-lysyl(N-epsilon-acetyl)amide, a group represented by the formula —NH—$(CH_2)_n$—$CHR^1R^2$; and a group represented by the formula —$NHR^3$, wherein n is an integer from 0 to 8; $R^1$ is selected from the group consisting of hydrogen, alkyl, cycloalkenyl, and cycloalkyl; $R^2$ is selected from the group consisting of hydrogen, alkoxy, alkyl, aryl, cycloalkenyl, cycloalkyl, heterocycle, and hydroxyl, with the proviso that when n is 0, $R^2$ is other than alkoxy or hydroxyl; and $R^3$ is selected from the group consisting of hydrogen, cycloalkenyl, cycloalkyl, and hydroxyl;

provided that when $Xaa_5$ is D-alloisoleucyl, $Xaa_6$ is threonyl and $Xaa_7$ is hydroxyl.

In a more preferred embodiment, the present invention provides a compound of formula (III), or a therapeutically acceptable salt thereof, wherein $Xaa_2$ is selected from the group consisting of threonyl and D-threonyl, $Xaa_3$ is selected from the group consisting of norvalyl and D-norvalyl, $Xaa_5$ is arginyl, and $Xaa_1$, $Xaa_4$, $Xaa_6$, and $Xaa_7$ are as defined for formula (II).

In another more preferred embodiment, the present invention provides a compound of formula (III), or a therapeutically acceptable salt thereof, wherein $Xaa_2$ is selected from the group consisting of allothreonyl, asparaginyl, aspartyl, homoseryl, sarcosyl, and tyrosyl, $Xaa_3$ is selected from the group consisting of norvalyl and D-norvalyl, $Xaa_5$ is arginyl, and $Xaa_1$, $Xaa_4$, $Xaa_6$, and $Xaa_7$ are as defined for formula (III).

In another more preferred embodiment, the present invention provides a compound of formula (III), or a therapeutically acceptable salt thereof, wherein $Xaa_2$ is selected from the group consisting of glutaminyl, glutamyl, N-methylglutamyl, lysyl(N-epsilon-acetyl), methionyl, seryl, and tryptyl, $Xaa_3$ is selected from the group consisting of norvalyl and D-norvalyl, $Xaa_5$ is arginyl, and $Xaa_1$, $Xaa_4$, $Xaa_6$, and $Xaa_7$ are as defined for formula (III).

In another more preferred embodiment, the present invention provides a compound of formula (III), or a therapeutically acceptable salt thereof, wherein $Xaa_3$ is selected from the group consisting of glutaminyl and D-glutaminyl, $Xaa_5$ is arginyl, and $Xaa_1$, $Xaa_2$, $Xaa_4$, $Xaa_6$, and $Xaa_7$ are as defined for formula (III).

In another more preferred embodiment, the present invention provides a compound of formula (III), or a therapeutically acceptable salt thereof, wherein $Xaa_3$ is selected from the group consisting of seryl and D-seryl, $Xaa_5$ is arginyl, and $Xaa_1$, $Xaa_2$, $Xaa_4$, $Xaa_6$, and $Xaa_7$ are as defined for formula (III).

In another more preferred embodiment, the present invention provides a compound of formula (III), or a therapeutically acceptable salt thereof, wherein $Xaa_3$ is selected from the group consisting of arginyl, asparaginyl, D-asparaginyl, citrullyl, glutamyl, D-leucyl, lysyl(N-epsilon-acetyl), lysyl (N-epsilon-nicotinyl), norleucyl, N-methylnorvalyl, threonyl, and tryptyl, $Xaa_5$ is arginyl, and $Xaa_1$, $Xaa_2$, $Xaa_4$, $Xaa_6$, and $Xaa_7$ are as defined for formula (III).

In another more preferred embodiment, the present invention provides a compound of formula (III), or a therapeutically acceptable salt thereof, wherein $Xaa_5$ is selected from the group consisting of D-alloisoleucyl, citrullyl, lysyl(N-epsilon-isopropyl), ornithyl, and 3-(3-pyridyl)alanyl, and $Xaa_1$, $Xaa_2$, $Xaa_3$, $Xaa_4$, $Xaa_6$, and $Xaa_7$ are as defined for formula (III).

In another embodiment, the present invention provides a pharmaceutical composition comprising a compound of formula (III), or a therapeutically acceptable salt thereof, in combination with a therapeutically acceptable carrier.

In another embodiment, the present invention provides a method of inhibiting angiogenesis in a mammal in recognized need of such treatment comprising administering to the mammal a therapeutically acceptable amount of a compound of formula (III) or a therapeutically acceptable salt thereof.

In another embodiment, the present invention provides a method of treating cancer in a mammal in recognized need of such treatment comprising administering to the mammal a therapeutically acceptable amount of a compound of formula (III) or a therapeutically acceptable salt thereof.

DETAILED DESCRIPTION OF THE INVENTION

As used herein, the singular forms "a", "an", and "the" include plural reference unless the context clearly dictates otherwise.

As used in the present specification the following terms have the meanings indicated:

The term "alkoxy," as used herein, represents an alkyl group attached to the parent molecular moiety through an oxygen atom.

The term "alkyl," as used herein, represents a monovalent group derived from a straight or branched chain saturated hydrocarbon by the removal of a hydrogen atom. Preferred alkyl groups for the present invention are alkyl groups having from one to six carbon atoms ($C_1$–$C_6$ alkyl). Alkyl groups of one to three carbon atoms ($C_1$–$C_3$ alkyl) are more preferred for the present invention.

The term "alkylcarbonyl," as used herein, represents an alkyl group attached to the parent molecular moiety through a carbonyl group.

The term "amino," as used herein, represents —$NR^aR^b$, wherein $R^a$ and $R^b$ are independently selected from the group consisting of hydrogen, alkyl, and alkylcarbonyl.

The term "aryl," as used herein, represents a phenyl group, or a bicyclic or tricyclic fused ring system wherein one or more of the fused rings is a phenyl group. Bicyclic fused ring systems are exemplified by a phenyl group fused to a cycloalkenyl group, as defined herein, a cycloalkyl group, as defined herein, or another phenyl group. Tricyclic fused ring systems are exemplified by a bicyclic fused ring system fused to a cycloalkenyl group, as defined herein, a cycloalkyl group, as defined herein or another phenyl group. Representative examples of aryl include, but are not limited to, anthracenyl, azulenyl, fluorenyl, indanyl, indenyl, naphthyl, phenyl, and tetrahydronaphthyl. The aryl groups of the present invention can be optionally substituted with one-, two, three, four, or five substituents independently selected from the group consisting of alkoxy, alkyl, carboxyl, halo, and hydroxyl.

The term "carbonyl," as used herein, represents —C(O)—.

The term "carboxyl," as used herein, represents —$CO_2H$.

The term "cycloalkenyl," as used herein, refers to a non-aromatic cyclic or bicyclic ring system having three to ten carbon atoms and one to three rings, wherein each five-membered ring has one double bond, each six-membered ring has one or two double bonds, each seven- and eight-membered ring has one to three double bonds, and each nine-to ten-membered ring has one to four double bonds. Examples of cycloalkenyl groups include cyclohexenyl, octahydronaphthalenyl, norbornylenyl, and the like. The cycloalkenyl groups of the present invention can be optionally substituted with one, two, three, four, or five substituents independently selected from the group consisting of alkoxy, alkyl, carboxyl, halo, and hydroxyl.

The term "cycloalkyl," as used herein, refers to a saturated monocyclic, bicyclic, or tricyclic hydrocarbon ring system having three to twelve carbon atoms. Examples of cycloalkyl groups include cyclopropyl, cyclopentyl, bicyclo [3.1.1]heptyl, adamantyl, and the like. The cycloalkyl groups of the present invention can be optionally substituted with one, two, three, four, or five substituents independently selected from the group consisting of alkoxy, alkyl, carboxyl, halo, and hydroxyl.

The term "halo," as used herein, represents F, Cl, Br, or I.

The term "heterocycle," as used herein, refers to a five-, six-, or seven-membered ring containing one, two, or three heteroatoms independently selected from the group consisting of nitrogen, oxygen, and sulfur. The five-membered ring has zero to two double bonds and the six- and seven-membered rings have zero to three double bonds. The term "heterocycle" also includes bicyclic groups in which the heterocycle ring is fused to an aryl group, as defined herein. The heterocycle groups of the present invention can be attached through a carbon atom or a nitrogen atom in the group. Examples of heterocycles include, but are not limited to, furyl, thienyl, pyrrolyl, pyrrolidinyl, oxazolyl, thiazolyl, imidazolyl, imidazolinyl, pyrazolyl, isoxazolyl, isothiazolyl, piperidinyl, morpholinyl, thiomorpholinyl, piperazinyl, pyridinyl, indolyl, indolinyl, and benzothienyl. The heterocycle groups of the present invention can be optionally substituted with one, two, three, or four substituents independently selected from the group consisting of alkoxy, alkyl, carboxyl, halo, and hydroxyl.

The term "hydroxyl," as used herein, represents —OH.

The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Unless indicated otherwise by a "D" prefix, e.g., D-Ala or NMe-D-Ile, the stereochemistry of the α-carbon of the amino acids and aminoacyl residues in peptides described in this specification and the appended claims is the natural or "L" configuration. The Cahn-Ingold-Prelog "R" and "S" designations are used to specify the stereochemistry of chiral centers in certain acyl substituents at the N-terminus of the peptides of this invention. The designation "R,S" is meant to indicate a racemic mixture of the two enantiomeric forms.

All peptide sequences are written according to the generally accepted convention whereby the α-N-terminal amino acid residue is on the left and the α-C-terminal is on the right. As used herein, the term "α-N-terminus" refers to the free α-amino group of an amino acid in a peptide, and the term "α-C-terminus" refers to the free α-carboxylic acid terminus of an amino acid in a peptide.

For the most part, the names on naturally occurring and non-naturally occurring aminoacyl residues used herein follow the naming conventions suggested by the IUPAC Commission on the Nomenclature of Organic chemistry and the IUPAC-IUB Commission on Biochemical Nomenclature. To the extent that the names and abbreviations of amino acids and aminoacyl residues employed in this specification and appended claims differ from those suggestions, they will be made clear to the reader. Some abbreviations useful in describing the invention are defined below in the following Table 1.

TABLE 1

| Abbreviation | Definition |
|---|---|
| N-Ac | N-acetyl |
| Ala | alanyl |
| bAla | β-alanyl |
| AlaNH$_2$ | alanylamide |
| aIle | alloisoleucyl |
| alloThr | allothreonyl |
| alloThr(O-tBu) | allothreonyl(O-t-butyl) |
| AllylGly | allylglycyl |
| Arg | arginyl |
| Arg(Pmc) | arginyl(N$^G$-2,2,5,7,8-pentamethylchroman-6-sulfonyl) |
| Fmoc-Arg(Pbf)-OH | N-Fmoc-N$^G$-(2,2,4,6,7-pentamethyldihydrobenzofuran-5-sulfonyl)arginine |
| Asn | asparaginyl |
| Asn(Trt) | asparaginyl(trityl) |
| Asp | aspartyl |
| Asp(O-tBu) | aspartyl(O-t-butyl) |
| Cit | citrullyl |
| Fmoc | 9-fluorenylmethyloxycarbonyl |
| Gln | glutaminyl |
| Gln(Trt) | glutaminyl(trityl) |
| Glu | glutamyl |
| Glu(O-tBu) | glutamyl(O-t-butyl) |
| NMeGlu | N-methylglutamyl |
| Gly | glycyl |
| His | histidyl |
| His(Trt) | histidyl(trityl) |
| Hphe | homophenylalanyl |
| Hser | homoseryl |
| Hser(Trt) | homoseryl(trityl) |
| Ile | isoleucyl |
| Leu | leucyl |
| Lys(Ac) | lysyl(N-epsilon-acetyl) |
| Lys(Boc) | lysyl(N-epsilon-t-butoxycarbonyl) |
| Lys(Isp) | lysyl(N-epsilon-isopropyl) |
| Lys(Nic) | lysyl(N-epsilon-nicotinyl) |
| Met | methionyl |
| N-3Mev | N-3-methylvaleryl |
| N-(6MeNic) | 6-methylnicotinyl |
| Nle | norleucyl |
| Nva | norvalyl |
| NMeNva | N-methylnorvalyl |
| Orn | ornithyl |
| Orn(Ac) | ornithyl(N-delta-acetyl) |
| Orn(Boc) | ornithyl(t-butoxycarbonyl) |
| 3-Pal | 3-(3-pyridyl)alanyl |
| Pen | penicillaminyl |
| Pen(Trt) | penicillaminyl(trityl) |
| 4ClPhe | 4-chlorophenylalanyl |
| Phe | phenylalanyl |
| Pro | prolyl |
| ProNHCH(CH$_3$)$_2$ | prolylisopropylamide |
| ProNHCH$_2$CH$_3$ | prolylethylamide |
| 3-Pal | 3-(3-pyridyl)alanyl |
| Sar | sarcosyl |
| Ser | seryl |
| Ser(O-tBu) | seryl(O-t-butyl) |
| Thr | threonyl |
| Thr(O-tBu) | threonyl(O-t-butyl) |
| Trp | tryptyl |
| Trp(Boc) | tryptyl(N-t-butoxycarbonyl) |
| Tyr | tyrosyl |

TABLE 1-continued

| Abbreviation | Definition |
|---|---|
| Tyr(O-tBu) | tyrosyl(O-t-butyl) |
| Val | valyl |

Compositions

The compounds of the invention, including but not limited to those specified in the examples, possess anti-angiogenic activity. As angiogenesis inhibitors, such compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e., chloromas, plasmacytomas and the plaques and tumors of mycosis fungicides and cutaneous T-cell lymphoma/leukemia) as well as in the treatment of lymphomas (both Hodgkin's and non-Hodgkin's lymphomas). In addition, these compounds may be useful in the prevention of metastases from the tumors described above either when used alone or in combination with radiotherapy and/or other chemotherapeutic agents.

Further uses include the treatment and prophylaxis of autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemagiomas, and capillary proliferation within atherosclerotic plaques; Osler-Webber Syndrome; myocardial angiogenesis; plaque neovascularization; telangiectasia; hemophiliac joints; angiofibroma; and wound granulation. Other uses include the treatment of diseases characterized by excessive or abnormal stimulation of endothelial cells, including not limited to intestinal adhesions, Crohn's disease, atherosclerosis, scleroderma, and hypertrophic scars, i.e., keloids. Another use is as a birth control agent, by inhibiting ovulation and establishment of the placenta. The compounds of the invention are also useful in the treatment of diseases that have angiogenesis as a pathologic consequence such as cat scratch disease (Rochele minutesalia quintosa) and ulcers (Helicobacter pylori). The compounds of the invention are also useful to reduce bleeding by administration prior to surgery, especially for the treatment of resectable tumors.

The compounds of the invention may be used in combination with other compositions and procedures for the treatment of diseases. For example, a tumor may be treated conventionally with surgery, radiation or chemotherapy combined with a peptide of the present invention and then a peptide of the present invention may be subsequently administered to the patient to extend the dormancy of micrometastases and to stabilize and inhibit the growth of any residual primary tumor. Additionally, the compounds of the invention may be combined with pharmaceutically acceptable excipients, and optionally sustained-release matrices, such as biodegradable polymers, to form therapeutic compositions.

A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho) esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

When used in the above or other treatments, a therapeutically effective amount of one of the compounds of the present invention may be employed in pure form or, where such forms exist, in therapeutically acceptable salt form. By a "therapeutically effective amount" of the compound of the invention is meant a sufficient amount of the compound to treat an angiogenic disease, (for example, to limit tumor growth or to slow or block tumor metastasis) at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination with the specific compound employed; and like factors well known in the medical arts. For example, it is well within the skill of the art to start doses of the compound at levels lower than those required to achieve the desired therapeutic effect and to gradually increase the dosage until the desired effect is achieved.

Alternatively, a compound of the present invention may be administered as pharmaceutical compositions containing the compound of interest in combination with one or more pharmaceutically acceptable excipients. A pharmaceutically acceptable carrier or excipient refers to a non-toxic solid, semi-solid or liquid filler, diluent, encapsulating material or formulation auxiliary of any type. The compositions may be administered parenterally, intracisternally, intravaginally, intraperitoneally, topically (as by powders, ointments, drops or transdermal patch), rectally, or bucally. The term "parenteral" as used herein refers to modes of administration which include intravenous, intramuscular, intraperitoneal, intrasternal, subcutaneous and intraarticular injection and infusion.

Pharmaceutical compositions for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Injectable depot forms are made by forming microencapsule matrices of the drug in biodegradable polymers such as polylactide-polyglycolide, poly(orthoesters), poly(anhydrides), and (poly)glycols, such as PEG. Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically-acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquefied gas propellant. The liquefied propellant medium and indeed the total composition is preferably such that the active ingredient does not dissolve therein to any substantial extent. The pressurized composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye. A compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the compounds of the invention may be injected directly into the vitreous and aqueous humour.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

While the compounds of the invention can be administered as the sole active pharmaceutical agent, they may also be used in combination with one or more agents which are conventionally administered to patients for treating angiogenic diseases. For example, the compounds of the invention are effective over the short term to make tumors more sensitive to traditional cytotoxic therapies such as chemicals and radiation. The compounds of the invention also enhance the effectiveness of existing cytotoxic adjuvant anti-cancer therapies. The compounds of the invention may also be combined with other antiangiogenic agents to enhance their effectiveness, or combined with other antiangiogenic agents and administered together with other cytotoxic agents. In particular, when used in the treatment of solid tumors, compounds of the invention may be administered with IL-12, retinoids, interferons, angiostatin, endostatin, thalidomide, thrombospondin-1, thrombospondin-2, captopryl, angioinhibins, TNP-470, pentosan polysulfate, platelet factor 4, LM-609, SU-5416, CM-101, Tecogalan, plasminogen-K-5, vasostatin, vitaxin, vasculostatin, squalamine, marimastat or other MMP inhibitors, anti-neoplastic agents such as alpha inteferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, cisplatin, taxol, etoposide/mechlorethamine, vincristine, prednisone and procarbazine), vincristine, vinblastine, and the like as well as with radiation.

Total daily dose of the compositions of the invention to be administered to a human or other mammal host in single or divided doses may be in amounts, for example, from 0.0001 to 300 mg/kg body weight daily and more usually 1 to 300 mg/kg body weight.

It will be understood that agents which can be combined with the compound of the present invention for the inhibition, treatment or prophylaxis of angiogenic diseases are not limited to those listed above, include in principle any agents useful for the treatment or prophylaxis of angiogenic diseases.

Determination of Biological Activity

In vitro Assay for Angiogenic Activity

The human microvascular endothelial (HMVEC) migration assay was run according to the procedure of S. S. Tolsma, O. V. Volpert, D. J. Good, W. F. Frazier, P. J. Polyerini and N. Bouck, *J. Cell Biol.* 1993, 122, 497–511.

The HMVEC migration assay was carried out using Human Microvascular Endothelial Cells-Dermal (single donor) and Human Microvascular Endothelial Cells, (neonatal). The HMVEC cells were starved overnight in DME containing 0.01% bovine serum albumin (BSA). Cells were then harvested with trypsin and resuspended in DME with 0.01% BSA at a concentration of $1.5 \times 10^6$ cells per mL. Cells were added to the bottom of a 48 well modified Boyden chamber (Nucleopore Corporation, Cabin John, Md.). The chamber was assembled and inverted, and cells were allowed to attach for 2 hours at 37° C. to polycarbonate chemotaxis membranes (5 μm pore size) that had been soaked in 0.01% gelatin overnight and dried. The chamber was then reinverted, and test substances (total volume of 50 μL), including activators, 15 ng/mL bFGF/VEGF, were added to the wells of the upper chamber. The apparatus was incubated for 4 hours at 37° C. Membranes were recovered, fixed and stained (Diff Quick, Fisher Scientific) and the number of cells that had migrated to the upper chamber per 3 high power fields counted. Background migration to DME+0.1 BSA was subtracted and the data reported as the number of cells migrated per 10 high power fields (400×) or, when results from multiple experiments were combined, as the percent inhibition of migration compared to a positive control.

Representative compounds described in Examples 1 to 154 inhibited human endothelial cell migration in the above assay by at least 55% when tested at a concentration of 10 nM. More preferred compounds inhibited human endothelial cell migration by approximately 80% to 98% when tested at a concentration of 1 nM, and most preferred compounds inhibited human endothelial cell migration by approximately 55% to 70% when tested at a concentration of 0.01 nM. As shown by these results, the compounds of the present invention demonstrate enhanced potency as compared to previously described antiangiogenic peptides.

Synthesis of the Peptides

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

The polypeptides of the present invention may be synthesized by many techniques that are known to those skilled in the art. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

Reagents, resins, amino acids, and amino acid derivatives are commercially available and can be purchased from chem-Impex International, Inc. (Wood Dale, Ill., U.S.A.) or Calbiochem-Novabiochem Corp. (San Diego, Calif., U.S.A.) unless otherwise noted herein.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compounds of the present invention involves solid phase peptide synthesis. In this particularly preferred method the α-amino function is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are 9-fluorenylmethyloxycarbonyl (Fmoc), t-butoxycarbonyl (Boc), benzyloxycarbonyl (Cbz), biphenylisopropyl-oxycarbonyl, t-amyloxycarbonyl, isobornyloxycarbonyl, (α,α)-dimethyl-3,5-dimethoxybenzyloxycarbonyl, O-nitrophenylsulfenyl, 2-cyano-t-butyloxycarbonyl, and the like. The 9-fluorenylmethyloxycarbonyl (Fmoc) protecting group is preferred.

Particularly preferred side chain protecting groups are: for arginine: $N^G$-2,2,5,7,8-pentamethylchroman-6-sulfonyl (Pmc), and 2,2,4,6,7-pentamethyldihydrobenzofuran-5-sulfonyl (Pbf); for asparagine: trityl (Trt); for aspartic acid: t-butyl (t-Bu); for glutamic acid: tert-butyl ester (O-tBu); for glutamine: trityl (Trt); for N-methylglutamine: t-butyl (t-Bu); for homoserine: trityl (Trt); for histidine: trityl (Trt); for lysine: t-butoxycarbonyl (Boc); for ornithyl: t-butoxycarbonyl (Boc), for penicillamine: trityl (Trt); for serine: t-butyl (t-Bu); for threonine and allothreonine: t-butyl (t-Bu); for tryptophan: t-butoxycarbonyl (Boc); and for tyrosine: t-butyl (t-Bu).

In the solid phase peptide synthesis method, the C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. The preferred solid support for synthesis of C-terminal carboxyl peptides is Sieber amide resin or Sieber ethylamide resin. The preferred solid support for C-terminal amide peptides is Sieber ethylamide resin available from Novabiochem Corporation.

The C-terminal amino acid is coupled to the resin by means of a coupling mediated by N,N'-dicyclohexylcarbodiimide (DCC), N,N'-diisopropylcarbodiimide (DIC), [O-(7-azabenzotriazol-1-yl)-1,1,3,3-tetramethyluronium hexafluorophosphate] (HATU), or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), N-methylmorpholine (NMM), benzotriazol-1-yloxy-tris(dimethylamino)phosphonium-hexafluorophosphate (BOP) or bis(2-oxo-3-oxazolidinyl) phosphine chloride (BOPCl), for about 1 to about 24 hours at a temperature of between 10° C. and 50° C. in a solvent such as dichloromethane or DMF.

When the solid support is Sieber amide or Sieber ethylamide resin, the Fmoc group is cleaved with a secondary amine, preferably piperidine, prior to coupling with the C-terminal amino acid as described above. The preferred reagents used in the coupling to the deprotected 4-(2',4'-dimethoxyphenyl-Fmoc-aminomethyl)phenoxyacetamido-ethyl resin are O-benzotriazol-1-yl-N,N,N',N'-tetramethyluroniumhexafluorophosphate (HBTU, 1 equiv.) with 1-hydroxybenzotriazole (HOBT, 1 equiv.), or [O-(7-azabenzotriazol-1-yl)-1,1,3,3-tetramethyluronium hexafluorophosphate] (HATU, 1 equiv.) with N-methylmorpholine (1 equiv.) in DMF.

The coupling of successive protected amino acids can be carried out in an automatic polypeptide synthesizer as is well known in the art. In a preferred embodiment, the α-amino function in the amino acids of the growing peptide chain are protected with Fmoc. The removal of the Fmoc protecting group from the N-terminal side of the growing peptide is accomplished by treatment with a secondary amine, preferably piperidine. Each protected amino acid is then introduced in about 3-fold molar excess and the coupling is preferably carried out in DMF. The coupling agent is normally O-benzotriazol-1-yl-N,N,N',N'-tetramethyluronium-hexafluorophosphate (HBTU, 1 equiv.) or [O-(7-azabenzo-triazol-1-yl)-1,1,3,3-tetramethyluronium hexafluorophosphate] (HATU, 1 equiv.) in the presence of N-methylmorpholine (NMM, 1 equiv.).

At the end of the solid phase synthesis, the polypeptide is removed from the resin and deprotected, either in succession or in a single operation. Removal of the polypeptide and deprotection can be accomplished in a single operation by treating the resin-bound polypeptide with a cleavage reagent, for example trifluoroacetic acid containing thianisole, water, or ethanedithiol.

In cases where the C-terminus of the polypeptide is an alkylamide, the resin is cleaved by aminolysis with an alkylamine. Alternatively, the peptide may be removed by transesterification, e.g., with methanol, followed by aminolysis or by direct transamidation. The protected peptide may be purified at this point or taken to the next step directly. The removal of the side chain protecting groups is accomplished using the cleavage cocktail described above.

The fully deprotected peptide is purified by a sequence of chromatographic steps employing any or all of the following types: ion exchange on a weakly basic resin in the acetate form; hydrophobic adsorption chromatography on underivatized polystyrene-divinylbenzene (for example, AMBERLITE® XAD); silica gel adsorption chromatography; ion exchange chromatography on carboxymethylcellulose; partition chromatography, e.g., on SEPHADEX® G-25, LH-20 or countercurrent distribution; high performance liquid chromatography (HPLC), especially reverse-phase HPLC on octyl- or octadecylsilyl-silica bonded phase column packing.

The foregoing may be better understood in light of the examples which are meant to describe compounds and process which can be carried out in accordance with the invention and are not intended as a limitation on the scope of the invention in any way.

Abbreviations which have been used the following examples are: DMF for N,N-dimethylformamide; HBTU for O-benzotriazol-1-yl-N,N,N',N'-tetramethyluronium-hexafluorophosphate; NMM for N-methylmorpholine; TFA for trifluoroacetic acid; NMP for N-methylpyrrolidinone; and HATU for [O-(7-azabenzotriazol-1-yl)-1,1,3,3-tetramethyluronium hexafluorophosphate].

EXAMPLE 1

N-Ac-D-Ile-Thr-Nva-Ile-Arg-ProNHCH$_2$CH$_3$

In the reaction vessel of a Rainin peptide synthesizer was placed Fmoc-Pro-Sieber ethylamide resin (0.25 g, 0.4 mmol/g loading). The resin was solvated with DMF and amino acids were coupled sequentially according to the following synthetic cycle:

(1) 3×1.5 minute washes with DMF;
(2) 2×15 minute deprotections using 20% piperidine;
(3) 6×3 minute washes with DMF;
(4) addition of amino acid;
(5) activation of amino acid with 0.4 M HBTU/NMM and coupling;
(6) 3×1.5 minute washes with DMF.

The protected amino acids were coupled to the resin in the following order:

| Protected Amino Acid | Coupling time |
| --- | --- |
| Fmoc-Arg(Pmc) | 30 minutes |
| Fmoc-Ile | 30 minutes |
| Fmoc-Nva | 30 minutes |
| Fmoc-Thr(O-tBu) | 30 minutes |
| Fmoc-D-Ile | 30 minutes |
| acetic acid | 30 minutes |

Upon completion of the synthesis the peptide was cleaved from the resin using a mixture of (95:2.5:2.5) TFA/anisole/water for 3 hours. The peptide solution was concentrated under vacuum and then precipitated with diethyl ether and collected by filtration. The crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Nva-Ile-Arg-ProNHCH$_2$CH$_3$ as the trifluoroacetate salt: R$_t$=3.38 minutes (gradient varying over 10 minutes from 20% to 80% acetonitrile/water containing 0.01% TFA); MS (ESI) m/e 767 (M+H)$^+$; Amino Acid Anal.: 2.06 Ile; 0.58 Thr; 1.01 Nva; 0.98 Arg; 1.04 Pro.

EXAMPLE 2

N-Ac-D-aIle-Thr-Nva-Ile-Arg-ProNHCH$_2$CH$_3$

The desired product was prepared by substituting Fmoc-D-aIle for Fmoc-D-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-aIle-Thr-Nva-Ile-Arg-ProNHCH$_2$CH$_3$ as the trifluoroacetate salt: R$_t$=2.52 minutes (gradient varying over 10 minutes from 20% to 80% acetonitrile/water containing 0.01% TFA); MS (ESI) m/e 767 (M+H)$^+$; Amino Acid Anal.: 2.11 Ile; 0.43 Thr; 0.99 Nva; 1.03 Arg; 1.02 Pro.

EXAMPLE 3

N-Ac-D-Ile-alloThr-Nva-Ile-Arg-ProNHCH$_2$CH$_3$

The desired product was prepared by substituting Fmoc-alloThr(O-tBu) for Fmoc-Thr(O-tBu) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-alloThr-Nva-Ile-Arg-ProNHCH$_2$CH$_3$ as the trifluoroacetate salt: $R_t$=2.56 minutes (gradient varying over 10 minutes from 20% to 80% acetonitrile/water containing 0.01% TFA); MS (ESI) m/e 767 (M+H)$^+$; Amino Acid Anal.: 2.02 Ile; 0.51 Thr; 0.96 Nva; 1.03 Arg; 1.07 Pro.

EXAMPLE 4

N-Ac-D-Ile-Thr-Gln-Ile-Arg-ProNHCH$_2$CH$_3$

The desired product was prepared by substituting Fmoc-Gln(Trt) for Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Gln-Ile-Arg-ProNHCH$_2$CH$_3$ as the trifluoroacetate salt: $R_t$=1.79 minutes (gradient varying over 10 minutes from 20% to 80% acetonitrile/water containing 0.01% TFA); MS (ESI) m/e 796 (M+H)$^+$; Amino Acid Anal.: 2.05 Ile; 0.44 Thr; 0.94 Glu; 1.02 Arg; 0.99 Pro.

EXAMPLE 5

N-Ac-D-aIle-Ser-Ser-Ile-Arg-ProNHCH$_2$CH$_3$

The desired product was prepared by substituting Fmoc-D-aIle for Fmoc-D-Ile and Fmoc-Ser(O-tBu) for both Fmoc-Thr(O-tBu) and Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-aIle-Ser-Ser-Ile-Arg-ProNHCH$_2$CH$_3$ as the trifluoroacetate salt: $R_t$=1.39 minutes (gradient varying over 10 minutes from 20% to 80% acetonitrile/water containing 0.01% TFA); MS (ESI) m/e 741 (M+H)$^+$; Amino Acid Anal.: 2.13 Ile; 0.48 Ser; 1.02 Arg; 1.04 Pro.

EXAMPLE 6

N-Ac-D-aIle-Thr-Ser-Ile-Arg-ProNHCH$_2$CH$_3$

The desired product was prepared by substituting Fmoc-D-aIle for Fmoc-D-Ile and Fmoc-Ser(O-tBu) for Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-aIle-Thr-Ser-Ile-Arg-ProNHCH$_2$CH$_3$ as the trifluoroacetate salt: $R_t$=1.73 minutes (gradient varying over 10 minutes from 20% to 80% acetonitrile/water containing 0.01% TFA); MS (ESI) m/e 755 (M+H)$^+$; Amino Acid Anal.: 2.10 Ile; 0.49 Thr; 0.21 Ser; 1.04 Arg; 1.02 Pro.

EXAMPLE 7

N-Ac-D-aIle-Tyr-Nva-Ile-Arg-ProNHCH$_2$CH$_3$

The desired product was prepared by substituting Fmoc-D-aIle for Fmoc-D-Ile and Fmoc-Tyr(O-tBu) for Fmoc-Thr(O-tBu) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-aIle-Tyr-Nva-Ile-Arg-ProNHCH$_2$CH$_3$ as the trifluoroacetate salt: $R_t$=2.89 minutes (gradient varying over 10 minutes from 20% to 80% acetonitrile/water containing 0.01% TFA); MS (ESI) m/e 829 (M+H)$^+$; Amino Acid Anal.: 2.06 Ile; 0.99 Tyr; 1.03 Nva; 1.01 Arg; 1.00 Pro.

EXAMPLE 8

N-Ac-D-aIle-Ser-Thr-Ile-Arg-ProNHCH$_2$CH$_3$

The desired product was prepared by substituting Fmoc-D-aIle for Fmoc-D-Ile, Fmoc-Ser(O-tBu) for Fmoc-Thr(O-tBu) and Fmoc-Thr(O-tBu) for Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-aIle-Ser-Thr-Ile-Arg-ProNHCH$_2$CH$_3$ as the trifluoroacetate salt: $R_t$=1.40 minutes (gradient varying over 10 minutes from 20% to 80% acetonitrile/water containing 0.01% TFA); MS (ESI) m/e 755 (M+H)$^+$; Amino Acid Anal.: 2.10 Ile; 0.19 Ser; 0.52 Thr; 1.02 Arg; 1.01 Pro.

EXAMPLE 9

N-(6MeNic)-D-Ile-Thr-Nva-Ile-Arg-ProNHCH$_2$CH$_3$

The desired product was prepared by substituting 6-methylnicotinic acid for acetic acid in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-(6-Me-Nicotinyl)-D-Ile-Thr-Nva-Ile-Arg-ProNHCH$_2$CH$_3$ as the trifluoroacetate salt: $R_t$=1.96 minutes (gradient varying over 10 minutes from 20% to 80% acetonitrile/water containing 0.01% TFA); MS (ESI) m/e 844 (M+H)$^+$; Amino Acid Anal.: 2.06 Ile; 0.50 Thr; 1.02 Nva; 1.04 Arg; 0.99 Pro.

EXAMPLE 10

N-Ac-D-Pro-Thr-Nva-Ile-Arg-ProNHCH$_2$CH$_3$

The desired product was prepared by substituting Fmoc-D-Pro for Fmoc-D-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Pro-Thr-Nva-Ile-Arg-ProNHCH$_2$CH$_3$ as the trifluoroacetate salt: $R_t$=1.62 minutes (gradient varying over 10 minutes from 20% to 80% acetonitrile/water containing 0.01% TFA); MS (ESI) m/e 751 (M+H)$^+$; Amino Acid Anal.: 1.01 Ile; 0.49 Thr; 0.98 Nva; 1.00 Arg; 2.08 Pro.

EXAMPLE 11

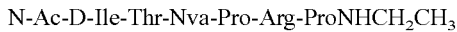
N-Ac-D-Ile-Thr-Nva-Pro-Arg-ProNHCH$_2$CH$_3$

The desired product was prepared by substituting Fmoc-Pro for Fmoc-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Nva-Pro-Arg-ProNHCH$_2$CH$_3$ as the trifluoroacetate salt: R$_f$=1.49 minutes (gradient varying over 10 minutes from 20% to 80% acetonitrile/water containing 0.01% TFA); MS (ESI) m/e 751 (M+H)$^+$; Amino Acid Anal.: 1.01 Ile; 0.54 Thr; 1.00 Nva; 1.00 Arg; 2.03 Pro.

EXAMPLE 12

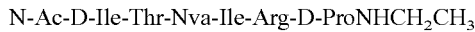
N-Ac-D-Ile-Thr-Nva-Ile-Arg-D-ProNHCH$_2$CH$_3$

The desired product was prepared by substituting Fmoc-D-Pro-Sieber ethylamide resin for Fmoc-Pro-Sieber ethylamide resin in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Nva-Ile-Arg-D-ProNHCH$_2$CH$_3$ as the trifluoroacetate salt: R$_f$=2.59 minutes (gradient varying over 10 minutes from 20% to 80% acetonitrile/water containing 0.01% TFA); MS (ESI) m/c 767 (M+H)$^+$; Amino Acid Anal.: 2.04 Ile; 0.47 Thr; 1.02 Nva; 1.06 Arg; 1.01 Pro.

EXAMPLE 13

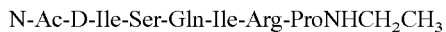
N-Ac-D-Ile-Ser-Gln-Ile-Arg-ProNHCH$_2$CH$_3$

The desired product was prepared by substituting Fmoc-Ser(O-tBu) for Fmoc-Thr(O-tBu) and Fmoc-Gln(Trt) for Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Ser-Gln-Ile-Arg-ProNHCH$_2$CH$_3$ as the trifluoroacetate salt: R$_f$=1.28 minutes (gradient varying over 10 minutes from 20% to 80% acetonitrile/water containing 0.01% TFA); MS (ESI) m/e 782 (M+H)$^+$; Amino Acid Anal.: 2.07 Ile; 0.22 Ser; 0.97 Glu; 1.03 Arg; 1.04 Pro.

EXAMPLE 14

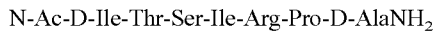
N-Ac-D-Ile-Thr-Ser-Ile-Arg-Pro-D-AlaNH$_2$

The desired product was prepared by substituting Fmoc-Ser(O-tBu) for Fmoc-Nva and Fmoc-D-Ala-Sieber amide resin for Fmoc-Pro-Sieber ethylamide resin and adding a coupling with Fmoc-Pro before the coupling with Fmoc-Arg(Pmc) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Ser-Ile-Arg-Pro-D-AlaNH$_2$ as the trifluoroacetate salt: R$_f$=1.35 minutes (gradient varying over 10 minutes from 20% to 80% acetonitrile/water containing 0.01% TFA); MS (ESI) m/e 798 (M+H)$^+$; Amino Acid Anal.: 2.02 Ile; 0.43 Thr; 0.24 Ser; 1.01 Arg; 0.99 Pro; 1.02 Ala.

EXAMPLE 15

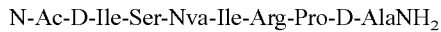
N-Ac-D-Ile-Ser-Nva-Ile-Arg-Pro-D-AlaNH$_2$

The desired product was prepared by substituting Fmoc-Ser(O-tBu) for Fmoc-Thr(O-tBu) and Fmoc-D-Ala-Sieber amide resin for Fmoc-Pro-Sieber ethylamide resin and adding a coupling with Fmoc-Pro before the coupling with Fmoc-Arg(Pmc) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Ser-Nva-Ile-Arg-Pro-D-AlaNH$_2$ as the trifluoroacetate salt: R$_f$=2.60 minutes (gradient varying over 10 minutes from 20% to 80% acetonitrile/water containing 0.01% TFA); MS (ESI) m/e 796 (M+H)$^+$; Amino Acid Anal.: 2.03 Ile; 0.19 Ser; 1.00 Nva; 1.01 Arg; 0.98 Pro; 1.02 Ala.

EXAMPLE 16

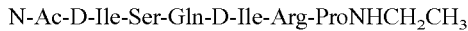
N-Ac-D-Ile-Ser-Gln-D-Ile-Arg-ProNHCH$_2$CH$_3$

The desired product was prepared by substituting Fmoc-Ser(O-tBu) for Fmoc-Thr(O-tBu), Fmoc-Gln(Trt) for Fmoc-Nva and Fmoc-D-Ile for Fmoc-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Ser-Gln-D-Ile-Arg-ProNHCH$_2$CH$_3$ as the trifluoroacetate salt: R$_f$=1.28 minutes (gradient varying over 10 minutes from 20% to 80% acetonitrile/water containing 0.01% TFA); MS (ESI) m/e 782 (M+H)$^+$; Amino Acid Anal.: 2.05 Ile; 0.29 Ser; 1.02 Glu; 1.03 Arg; 1.02 Pro.

EXAMPLE 17

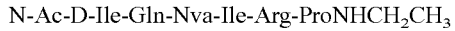
N-Ac-D-Ile-Gln-Nva-Ile-Arg-ProNHCH$_2$CH$_3$

The desired product was prepared by substituting Fmoc-Gln(Trt) for Fmoc-Thr(O-tBu) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Gln-Nva-Ile-Arg-ProNHCH$_2$CH$_3$ as the trifluoroacetate salt: R$_f$=1.45 minutes (gradient varying over 10 minutes from 20% to 80% acetonitrile/water containing 0.01% TFA); MS (ESI) m/e 794 (M+H)$^+$; Amino Acid Anal.: 2.10 Ile; 1.01 Glu; 1.02 Nva; 0.99 Arg; 0.98 Pro.

EXAMPLE 18

N-Ac-D-Ile-Thr-Nva-Ile-Arg-Pro-D-AlaNH$_2$

The desired product was prepared by substituting Fmoc-D-Ala-Sieber amide resin for Fmoc-Pro-Sieber ethylamide resin and adding a coupling with Fmoc-Pro before the coupling with Fmoc-Arg(Pmc) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Nva-Ile-Arg-Pro-D-AlaNH$_2$ as the trifluoroacetate salt: R$_f$=2.10 minutes (gradient varying over 10 minutes from 20% to 80% acetonitrile/water containing 0.01% TFA); MS (ESI) m/e 10 (M+H)$^+$; Amino Acid Anal.: 2.10 Ile; 0.49 Thr; 0.99 Nva; 1.00 Arg; 0.98 Pro; 1.02 Ala.

EXAMPLE 19

N-Ac-D-Leu-Thr-Nva-Ile-Arg-ProNHCH$_2$CH$_3$

The desired product was prepared by substituting Fmoc-D-Leu for Fmoc-D-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Leu-Thr-Nva-Ile-Arg-ProNHCH$_2$CH$_3$ as the trifluoroacetate salt: R$_t$=2.57 minutes (gradient varying over 10 minutes from 20% to 80% acetonitrile/water containing 0.01% TFA); MS (ESI) m/e 767 (M+H)$^+$; Amino Acid Anal.: 1.01 Leu; 0.51 Thr; 1.00 Nva; 1.04 Ile; 1.02 Arg; 1.04 Pro.

EXAMPLE 20

N-Ac-D-Leu-Ser-Nva-Ile-Arg-ProNHCH$_2$CH$_3$

The desired product was prepared by substituting Fmoc-D-Leu for Fmoc-D-Ile and Fmoc-Ser(O-tBu) for Fmoc-Thr(O-tBu) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Leu-Ser-Nva-Ile-Arg-ProNHCH$_2$CH$_3$ as the trifluoroacetate salt: R$_t$=2.50 minutes (gradient varying over 10 minutes from 20% to 80% acetonitrile/water containing 0.01% TFA); MS (ESI) m/e 753 (M+H)$^+$; Amino Acid Anal.: 1.01 Leu; 0.23 Ser; 1.03 Nva; 1.02 Ile; 1.02 Arg; 0.99 Pro.

EXAMPLE 21

N-Ac-D-Ile-Thr-Nva-D-Leu-Arg-ProNHCH$_2$CH$_3$

The desired product was prepared by substituting Fmoc-D-Leu for Fmoc-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Nva-D-Leu-Arg-ProNHCH$_2$CH$_3$ as the trifluoroacetate salt: R$_t$=2.71 minutes (gradient varying over 10 minutes from 20% to 80% acetonitrile/water containing 0.01% TFA); MS (ESI) m/e 767 (M+H)$^+$; Amino Acid Anal.: 1.02 Ile; 0.55 Thr; 1.01 Nva; 1.00 Leu; 1.01 Arg; 1.01 Pro.

EXAMPLE 22

N-Ac-D-Ile-Thr-Nva-D-Ile-Arg-ProNHCH$_2$CH$_3$

The desired product was prepared by substituting Fmoc-D-Ile for Fmoc-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Nva-D-Ile-Arg-ProNHCH$_2$CH$_3$ as the trifluoroacetate salt: R$_t$=2.61 minutes (gradient varying over 10 minutes from 20% to 80% acetonitrile/water containing 0.01% TFA); MS (ESI) m/c 767 (M+H)$^+$; Amino Acid Anal.: 2.04 Ile; 0.42 Thr; 1.02 Nva; 1.00 Arg; 1.03 Pro.

EXAMPLE 23

N-Ac-D-Ile-Tyr-Nva-D-Ile-Arg-ProNHCH$_2$CH$_3$

The desired product was prepared by substituting Fmoc-Tyr(O-tBu) for Fmoc-Thr(O-tBu) and Fmoc-D-Ile for Fmoc-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Tyr-Nva-D-Ile-Arg-ProNHCH$_2$CH$_3$ as the trifluoroacetate salt: R$_t$=2.94 minutes (gradient varying over 10 minutes from 20% to 80% acetonitrile/water containing 0.01% TFA); MS (ESI) m/e 829 (M+H)$^+$; Amino Acid Anal.: 2.09 Ile; 0.96 Tyr; 1.03 Nva; 0.97 Arg; 1.01 Pro.

EXAMPLE 24

N-Ac-D-Ile-Thr-Trp-D-Ile-Arg-ProNHCH$_2$CH$_3$

The desired product was prepared by substituting Fmoc-Trp(Boc) for Fmoc-Nva and Fmoc-D-Ile for Fmoc-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Trp-D-Ile-Arg-ProNHCH$_2$CH$_3$ as the trifluoroacetate salt: R$_t$=3.17 minutes (gradient varying over 10 minutes from 20% to 80% acetonitrile/water containing 0.01% TFA); MS (ESI) m/e 854 (M+H)$^+$.

EXAMPLE 25

N-Ac-D-aIle-Thr-Trp-Ile-Arg-ProNHCH$_2$CH$_3$

The desired product was prepared by substituting Fmoc-D-aIle for Fmoc-D-Ile and Fmoc-Trp(Boc) for Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-aIle-Thr-Trp-Ile-Arg-ProNHCH$_2$CH$_3$ as the trifluoroacetate salt: R$_t$=3.06 minutes (gradient varying over 10 minutes from 20% to 80% acetonitrile/water containing 0.01% TFA); MS (ESI) m/e 854 (M+H)$^+$.

EXAMPLE 26

N-Ac-D-Ile-Thr-Trp-Ile-Arg-Pro-D-AlaNH$_2$

The desired product was prepared by substituting Fmoc-Trp(Boc) for Fmoc-Nva and Fmoc-D-Ala-Sieber amide resin for Fmoc-Pro-Sieber ethylamide resin and adding a coupling with Fmoc-Pro before the coupling with Fmoc-Arg(Pmc) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Trp-Ile-Arg-Pro-D-AlaNH$_2$ as the trifluoroacetate salt: R$_t$=2.97 minutes (gradient varying over 10 minutes from 20% to 80% acetonitrile/water containing 0.01% TFA); MS (ESI) m/e 897 (M+H)$^+$.

EXAMPLE 27

N-Ac-D-Ile-Thr-Nva-Ile-Arg-Pro-D-Lys(Ac)NH$_2$

The desired product was prepared by substituting Fmoc-D-Lys(Ac)-Sieber-amide resin for Fmoc-Pro-Sieber ethylamide resin and adding a coupling with Fmoc-Pro before the coupling with Fmoc-Arg(Pmc) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Nva-Ile-Arg-Pro-D-Lys(Ac)NH$_2$ as the trifluoroacetate salt: $R_t$=2.32 minutes (gradient varying over 10 minutes from 20% to 80% acetonitrile/water containing 0.01% TFA); MS (ESI) m/e 909 (M+H)$^+$.

EXAMPLE 28

N-Ac-D-Ile-Thr-Gln-Ile-Arg-Pro-D-AlaNH$_2$

The desired product was prepared by substituting Fmoc-Gln(Trt) for Fmoc-Nva and Fmoc-D-Ala-Sieber amide resin for Fmoc-Pro-Sieber ethylamide resin and adding a coupling with Fmoc-Pro before the coupling with Fmoc-Arg(Pmc) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Gln-Ile-Arg-Pro-D-AlaNH$_2$ as the trifluoroacetate salt: $R_t$=1.34 minutes (gradient varying over 10 minutes from 20% to 80% acetonitrile/water containing 0.01% TFA); MS (ESI) m/e 839 (M+H)$^+$.

EXAMPLE 29

N-Ac-D-Ile-Thr-Nva-D-Lys(Ac)-Arg-ProNHCH$_2$CH$_3$

The desired product was prepared by substituting Fmoc-D-Lys(Ac) for Fmoc-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Nva-D-Lys(Ac)-Arg-ProNHCH$_2$CH$_3$ as the trifluoroacetate salt: $R_t$=1.58 minutes (gradient varying over 10 minutes from 20% to 80% acetonitrile/water containing 0.01% TFA); MS (ESI) m/e 824 (M+H)$^+$.

EXAMPLE 30

N-Ac-D-Ile-Thr-Nva-Lys(Ac)-Arg-ProNHCH$_2$CH$_3$

The desired product was prepared by substituting Fmoc-Lys(Ac) for Fmoc-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Nva-Lys(Ac)-Arg-ProNHCH$_2$CH$_3$ as the trifluoroacetate salt: $R_t$=1.51 minutes (gradient varying over 10 minutes from 20% to 80% acetonitrile/water containing 0.01% TFA); MS (ESI) m/e 824 (M+H)$^+$.

EXAMPLE 31

N-Ac-D-Ile-Lys(Ac)-Nva-Ile-Arg-ProNHCH$_2$CH$_3$

The desired product was prepared by substituting Fmoc-Lys(Ac) for Fmoc-Thr(O-tBu) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Lys(Ac)-Nva-Ile-Arg-ProNHCH$_2$CH$_3$ as the trifluoroacetate salt: $R_t$=2.51 minutes (gradient varying over 10 minutes from 20% to 80% acetonitrile/water containing 0.01% TFA); MS (ESI) m/e 836 (M+H)$^+$.

EXAMPLE 32

N-Ac-D-Ile-Thr-Nva-Ile-His-ProNHCH$_2$CH$_3$

The desired product was prepared by substituting Fmoc-His(Trt) for Fmoc-Arg(Pmc) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Nva-Ile-His-ProNHCH$_2$CH$_3$ as the trifluoroacetate salt: $R_t$=2.45 minutes (gradient varying over 10 minutes from 20% to 80% acetonitrile/water containing 0.01% TFA); MS (ESI) m/e 748 (M+H)$^+$.

EXAMPLE 33

N-Ac-D-Hphe-Thr-Nva-Ile-Arg-ProNHCH$_2$CH$_3$

The desired product was prepared by substituting Fmoc-D-Hphe for Fmoc-D-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Hphe-Thr-Nva-Ile-Arg-ProNHCH$_2$CH$_3$ as the trifluoroacetate salt: $R_t$=3.12 minutes (gradient varying over 10 minutes from 20% to 80% acetonitrile/water containing 0.01% TFA); MS (ESI) m/e 815 (M+H)$^+$.

EXAMPLE 34

N-Ac-D-4ClPhe-Thr-Nva-Ile-Arg-ProNHCH$_2$CH$_3$

The desired product was prepared by substituting Fmoc-D-4ClPhe for Fmoc-D-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-4ClPhe-Thr-Nva-Ile-Arg-ProNHCH$_2$CH$_3$ as the trifluoroacetate salt: $R_t$=3.28 minutes (gradient varying over 10 minutes from 20% to 80% acetonitrile/water containing 0.01% TFA); MS (ESI) m/e 835 (M+H)$^+$.

EXAMPLE 35

N-Ac-D-Pen-Thr-Nva-Ile-Arg-ProNHCH$_2$CH$_3$

The desired product was prepared by substituting Fmoc-D-Pen(Trt) for Fmoc-D-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Pen-Thr-Nva-Ile-Arg-ProNHCH$_2$CH$_3$ as the trifluoroacetate salt: $R_t$=2.41 minutes (gradient varying over 10 minutes from 20% to 80% acetonitrile/water containing 0.01% TFA); MS (ESI) m/e 785 (M+H)$^+$.

EXAMPLE 36

N-Ac-D-Ile-Met-Nva-Ile-Arg-ProNHCH$_2$CH$_3$

The desired product was prepared by substituting Fmoc-Met for Fmoc-Thr(O-tBu) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Met-Nva-Ile-Arg-ProNHCH$_2$CH$_3$ as the trifluoroacetate salt: $R_t$=3.11 minutes (gradient varying over 10 minutes from 20% to 80% acetonitrile/water containing 0.01% TFA); MS (ESI) m/e 797 (M+H)$^+$.

EXAMPLE 37

N-Ac-D-Ile-Asp-Nva-Ile-Arg-ProNHCH$_2$CH$_3$

The desired product was prepared by substituting Fmoc-Asp(O-tBu) for Fmoc-Thr(O-tBu) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Asp-Nva-Ile-Arg-ProNHCH$_2$CH$_3$ as the trifluoroacetate salt: $R_t$=2.32 minutes (gradient varying over 10 minutes from 20% to 80% acetonitrile/water containing 0.01% TFA); MS (ESI) m/e 781 (M+H)$^+$.

EXAMPLE 38

N-Ac-D-Ile-Thr-Nva-Ile-3-Pal-ProNHCH$_2$CH$_3$

The desired product was prepared by substituting Fmoc-3-Pal for Fmoc-Arg(Pmc) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Nva-Ile-3-Pal-ProNHCH$_2$CH$_3$ as the trifluoroacetate salt: $R_t$=2.45 minutes (gradient varying over 10 minutes from 20% to 80% acetonitrile/water containing 0.01% TFA); MS (ESI) m/e 759 (M+H)$^+$.

EXAMPLE 39

N-Ac-D-Ile-Thr-Nva-Ile-D-Arg-ProNHCH$_2$CH$_3$

The desired product was prepared by substituting Fmoc-D-Arg(Pmc) for Fmoc-Arg(Pmc) in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Nva-Ile-D-Arg-ProNHCH$_2$CH$_3$ as the trifluoroacetate salt: $R_t$=2.71 minutes (gradient varying over 10 minutes from 20% to 80% acetonitrile/water containing 0.01% TFA); MS (ESI) m/e 767 (M+H)$^+$.

EXAMPLE 40

N-Ac-D-Ile-Thr-Nle-Ile-Arg-ProNHCH$_2$CH$_3$

The desired product was prepared by substituting Fmoc-Nle for Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-Nle-Ile-Arg-ProNHCH$_2$CH$_3$ as the trifluoroacetate salt: $R_t$=2.82 minutes (gradient varying over 10 minutes from 20% to 80% acetonitrile/water containing 0.01% TFA); MS (ESI) m/e 781 (M+H)$^+$.

EXAMPLE 41

N-Ac-D-Ile-Thr-D-Gln-Ile-Arg-ProNHCH$_2$CH$_3$

The desired product was prepared by substituting Fmoc-D-Gln(Trt) for Fmoc-Nva in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-Thr-D-Gln-Ile-Arg-ProNHCH$_2$CH$_3$ as the trifluoroacetate salt: $R_t$=1.60 minutes (gradient varying over 10 minutes from 20% to 80% acetonitrile/water containing 0.01% TFA); MS (ESI) m/e 796 (M+H)$^+$.

EXAMPLE 42

N-Ac-D-Ile-alloThr-Nva-Pro-Arg-ProNHCH$_2$CH$_3$

The desired product was prepared by substituting Fmoc-alloThr(O-tBu) for Fmoc-Thr(O-tBu) and Fmoc-Pro for Fmoc-Ile in Example 1. After workup the crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-D-Ile-alloThr-Nva-Pro-Arg-ProNHCH$_2$CH$_3$ as the trifluoroacetate salt: $R_t$=1.52 minutes (gradient varying over 10 minutes from 20% to 80% acetonitrile/water containing 0.01% TFA); MS (ESI) m/e 751 (M+H)$^+$.

EXAMPLE 43

N-Ac-Thr-Nva-Ile-Arg-ProNHCH$_2$CH$_3$ (SEQ ID NO:4)

In the reaction vessel of a Rainin peptide synthesizer Fmoc-Pro-Sieber ethylamide resin (0.25 g, 0.4 mmol/g loading) was placed. The resin was solvated with DMF and amino acids were coupled sequentially according to the following synthetic cycle:
(1) 3×1.5 minute washes with DMF;
(2) 2×15 minute deprotections using 20% piperidine;
(3) 6×3 minute washes with DMF;
(4) addition of amino acid;
(5) activation of amino acid with 0.4 M HBTU/NMM and coupling;
(6) 3×1.5 minute washes with DMF.

The protected amino acids were coupled to the resin in the following order:

| Protected Amino Acid | Coupling time |
| --- | --- |
| Fmoc-Arg(Pmc) | 30 minutes |
| Fmoc-Ile | 30 minutes |
| Fmoc-Nva | 30 minutes |
| Fmoc-Thr(O-tBu) | 30 minutes |
| acetic acid | 30 minutes |

Upon completion of the synthesis the peptide was cleaved from the resin using a mixture of (95:2.5:2.5) TFA/anisole/water for 3 hours. The peptide solution was concentrated under vacuum and then precipitated with diethyl ether and collected by filtration. The crude peptide was purified by HPLC using a C-18 column and with a solvent mixture varying over 50 minutes from 5% to 100% acetonitrile/water containing 0.01% TFA. The pure fractions were lyophilized to provide N-Ac-Thr-Nva-Ile-Arg-ProNHCH$_2$CH$_3$ as the trifluoroacetate salt: R$_t$=1.16 minutes (gradient varying over 10 minutes from 20% to 80% acetonitrile/water containing 0.01% TFA); MS (ESI) m/e 654 (M+H)$^+$; Amino Acid Anal.: 0.49 Thr; 1.02 Nva; 0.99 Ile; 1.01 Arg; 1.04 Pro.

EXAMPLE 44

N-Ac-alloThr-Nva-Ile-Arg-ProNHCH$_2$CH$_3$ (SEQ ID NO:5)

The desired product was prepared by substituting Fmoc-alloThr(O-tBu) for Fmoc-Thr(O-tBu) in Example 43. After workup the crude peptide was purified by HPLC using a C-18 column and a solvent system varying in gradient from 5% to 100% acetonitrile/water containing 0.01% TFA over 50 minutes. The pure fractions were lyophilized to provide N-Ac-alloThr-Nva-Ile-Arg-ProNHCH$_2$CH$_3$ as the trifluoracetate salt: R$_t$=1.07 minutes (gradient varying over 10 minutes from 20% to 80% acetonitrile/water containing 0.01% TFA); MS (ESI) m/e 654 (M+H)$^+$; Amino Acid Anal.: 0.57 Thr; 1.00 Nva; 1.02 Ile; 0.98 Arg; 1.04 Pro.

EXAMPLE 45

N-Ac-Thr-Gln-Ile-Arg-ProNHCH$_2$CH$_3$ (SEQ ID NO:6)

The desired product was prepared by substituting Fmoc-Gln(Trt) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Gln-Ile-Arg-ProNHCH$_2$CH$_3$ as the trifluoracetate salt: R$_t$=1.01 minutes (gradient varying over 10 minutes from 20% to 80% acetonitrile/water containing 0.01% TFA); MS (ESI) m/e 683.5 (M+H)$^+$; Amino Acid Anal.: 0.49 Thr; 1.01 Glu; 0.98 Ile; 1.05 Arg; 1.00 Pro.

EXAMPLE 46

N-(6MeNic)-Thr-Nva-Ile-Arg-ProNHCH$_2$CH$_3$ (SEQ ID NO:7)

The desired product was prepared by substituting 6-methylnicotinic acid for acetic acid in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N(6MeNic)-Thr-Nva-Ile-Arg-ProNHCH$_2$CH$_3$ as the trifluoracetate salt: R$_t$=0.94 minutes (gradient varying over 10 minutes from 20% to 80% acetonitrile/water containing 0.01% TFA); MS (ESI) m/e 731.5 (M+H)$^+$; Amino Acid Anal.: 0.51 Thr; 1.00 Nva; 1.01 Ile; 1.10 Arg; 1.03 Pro.

EXAMPLE 47

N-Ac-Ser-Ser-Ile-Arg-ProNHCH$_2$CH$_3$ (SEQ ID NO:8)

The desired product was prepared by substituting Fmoc-Ser(O-tBu) for Fmoc-Thr(O-tBu) and Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Ser-Ser-Ile-Arg-ProNHCH$_2$CH$_3$ as the trifluoracetate salt: R$_t$=3.34 minutes (gradient varying over 10 minutes from 20% to 80% acetonitrile/water containing 0.01% TFA); MS (ESI) m/e 628.3 (M+H)$^+$; Amino Acid Anal.: 0.43 Ser; 0.96 Ile; 1.00 Arg; 1.04 Pro.

EXAMPLE 48

N-Ac-Thr-Ser-Ile-Arg-ProNHCH$_2$CH$_3$ (SEQ ID NO:9)

The desired product was prepared by substituting Fmoc-Ser(O-tBu) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Ser-Ile-Arg-ProNHCH$_2$CH$_3$ as the trifluoracetate salt: R$_t$=3.52 minutes (gradient varying over 10 minutes from 20% to 80% acetonitrile/water containing 0.01% TFA); MS (ESI) m/e 642.3 (M+H)$^+$; Amino Acid Anal.: 0.55 Thr; 0.23 Ser; 0.96 Ile; 0.98 Arg; 1.04 Pro.

EXAMPLE 49

N-Ac-Thr-Nva-Ile-Arg-Pro-D-AlaNH$_2$

The desired product was prepared by substituting Fmoc-D-Ala-Sieber amide resin for Fmoc-Pro-Sieber ethylamide resin and adding a coupling with Fmoc-Pro before the coupling with Fmoc-Arg(Pmc) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Nva-Ile-Arg-Pro-D-AlaNH$_2$ as the trifluoracetate salt: R$_t$=3.94 minutes (gradient varying over 10 minutes from 20% to 80% acetonitrile/water containing 0.01% TFA); MS (ESI) m/e 697.3 (M+H)$^+$; Amino Acid Anal.: 0.56 Thr; 0.92 Nva; 0.97 Ile; 0.85 Arg; 1.09 Pro; 1.09 Ala.

EXAMPLE 50

N-Ac-Thr-Nva-D-Ile-Arg-ProNHCH$_2$CH$_3$

The desired product was prepared by substituting Fmoc-D-Ile for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Nva-D-Ile-Arg-ProNHCH$_2$CH$_3$ as the trifluoracetate salt: R$_f$=4.59 minutes (gradient varying over 10 minutes from 20% to 80% acetonitrile/water containing 0.01% TFA); MS (ESI) m/e 654.4 (M+H)$^+$; Amino Acid Anal.: 0.51 Thr; 0.84 Nva; 1.03 Ile; 0.97 Arg; 1.01 Pro.

EXAMPLE 51

N-Ac-Thr-NMeNva-Ile-Arg-ProNHCH$_2$CH$_3$ (SEQ ID NO: 10)

The desired product was prepared by substituting Fmoc-NMeNva for Fmoc-Nva and using HATU as the activator in the Fmoc-NMeNva coupling in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-NMeNva-Ile-Arg-ProNHCH$_2$CH$_3$ as the trifluoracetate salt: R$_f$=4.305 minutes (gradient varying over 10 minutes from 20% to 80% acetonitrile/water containing 0.01% TFA); MS (ESI) m/e 668.4 (M+H)$^+$; Amino Acid Anal.: 0.22 Thr; 1.01 Ile; 0.95 Arg; 1.03 Pro.

EXAMPLE 52

N-Ac-Thr-Gln-Ile-Arg-Pro-D-AlaNH$_2$

The desired product was prepared by substituting Fmoc-Gln(Trt) for Fmoc-Nva, Fmoc-D-Ala-Sieber amide resin for Fmoc-Pro-Sieber ethylamide resin, and by adding a coupling with Fmoc-Pro before the coupling with Fmoc-Arg (Pmc) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Gln-Ile-Arg-Pro-D-AlaNH$_2$ as the trifluoracetate salt: R$_f$=3.375 minutes (gradient varying over 10 minutes from 20% to 80% acetonitrile/water containing 0.01% TFA); MS (ESI) m/e 726.4 (M+H)$^+$; Amino Acid Anal.: 0.51 Thr; 0.55 Glu; 0.96 Ile; 0.82 Arg; 1.11 Pro; 1.12 Ala.

EXAMPLE 53

N-Ac-Tyr-Nva-Ile-Arg-ProNHCH$_2$CH$_3$ (SEQ ID NO: 11)

The desired product was prepared by substituting Fmoc-Tyr(O-tBu) for Fmoc-Thr(O-tBu) in Example 43. After workup the crude peptide was purified by HPLC using a C-18 column and a solvent system varying in gradient from 5% to 100% acetonitrile/water containing 0.01% TFA. The pure fractions were lyophilized to provide N-Ac-Tyr-Nva-Ile-Arg-ProNHCH$_2$CH$_3$ as the trifluoracetate salt: R$_f$=4.845 minutes (gradient varying over 10 minutes from 20% to 80% acetonitrile/water containing 0.01% TFA); MS (ESI) m/e 716.4 (M+H)$^+$; Amino Acid Anal.: 0.94 Tyr; 0.85 Nva; 0.96 Ile; 1.02 Arg; 1.02 Pro.

EXAMPLE 54

N-Ac-Ser-Gln-Ile-Arg-ProNHCH$_2$CH$_3$ (SEQ ID NO:12)

The desired product was prepared by substituting Fmoc-Ser(O-tBu) for Fmoc-Thr(O-tBu) and Fmoc-Gln(Trt) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Ser-Gln-Ile-Arg-ProNHCH$_2$CH$_3$ as the trifluoracetate salt: R$_f$=3.377 minutes (gradient varying over 10 minutes from 20% to 80% acetonitrile/water containing 0.01% TFA); MS (ESI) m/e 669.3 (M+H)$^+$; Amino Acid Anal.: 0.14 Ser; 0.79 Glu; 0.93 Ile; 0.98 Arg; 1.04 Pro.

EXAMPLE 55

N-Ac-Thr-Nva-Lys(Ac)-Arg-ProNHCH$_2$CH$_3$ (SEQ ID NO:13)

The desired product was prepared by substituting Fmoc-Lys(Ac) for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Nva-Lys(Ac)-Arg-ProNHCH$_2$CH$_3$ as the trifluoracetate salt: R$_f$=3.556 minutes (gradient varying over 10 minutes from 20% to 80% acetonitrile/water containing 0.01% TFA); MS (ESI) m/e 711.4 (M+H)$^+$; Amino Acid Anal.: 0.52 Thr; 0.84 Nva; 1.02 Lys; 0.97 Arg; 1.01 Pro.

EXAMPLE 56

N-Ac-Ser-Thr-Ile-Arg-ProNHCH$_2$CH$_3$ (SEQ ID NO:14)

The desired product was prepared by substituting Fmoc-Ser(O-tBu) for Fmoc-Thr(O-tBu) and Fmoc-Thr(O-tBu) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Ser-Thr-Ile-Arg-ProNHCH$_2$CH$_3$ as the trifluoracetate salt: R$_f$=3.388 minutes (gradient varying over 10 minutes from 20% to 80% acetonitrile/water containing 0.01% TFA); MS (ESI) m/e 642.3 (M+H)$^+$; Amino Acid Anal.: 0.43 Thr; 0.19 Ser; 0.98 Ile; 0.97 Arg; 1.06 Pro.

EXAMPLE 57

N-Ac-Tyr-Nva-D-Ile-Arg-ProNHCH$_2$CH$_3$

The desired product was prepared by substituting Fmoc-Tyr(O-tBu) for Fmoc-Thr(O-tBu) and Fmoc-D-Ile for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Tyr-Nva-D-Ile-Arg-ProNHCH$_2$CH$_3$ as the trifluoracetate salt: R$_f$=5.103 minutes (gradient varying over 10 minutes from 20% to 80% acetonitrile/water containing 0.01% TFA); MS (ESI) m/e 716.4 (M+H)$^+$; Amino Acid Anal.: 0.94 Tyr; 0.85 Nva; 1.00 Ile; 1.04 Arg; 1.02 Pro.

EXAMPLE 58

N-Ac-NMeGlu-Nva-Ile-Arg-ProNHCH$_2$CH$_3$ (SEQ ID NO: 15)

The desired product was prepared by substituting Fmoc-NMeGlu(t-Bu) for Fmoc-Thr(O-tBu) and using HATU as activator in the Fmoc-NMeGlu(t-Bu) coupling in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-NMeGlu-Nva-Ile-Arg-ProNHCH$_2$CH$_3$ as the trifluoracetate salt: $R_f$=4.51 minutes (gradient varying over 10 minutes from 20% to 80% acetonitrile/water containing 0.01% TFA); MS (ESI) m/e 696.4 (M+H)$^+$.

EXAMPLE 59

N-Ac-Met-Nva-Ile-Arg-ProNHCH$_2$CH$_3$ (SEQ ID NO: 16)

The desired product was prepared by substituting Fmoc-Met for Fmoc-Thr(O-tBu) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Met-Nva-Ile-Arg-ProNHCH$_2$CH$_3$ as the trifluoracetate salt: $R_f$=4.913 minutes (gradient varying over 10 minutes from 20% to 80% acetonitrile/water containing 0.01% TFA); MS (ESI) m/e 684.4 (M+H)$^+$; Amino Acid Anal.: 0.91 Met; 0.90 Nva; 1.01 Ile; 1.03 Arg; 1.05 Pro.

EXAMPLE 60

N-Ac-Lys(Ac)-Nva-Ile-Arg-ProNHCH$_2$CH$_3$ (SEQ ID NO: 17)

The desired product was prepared by substituting Fmoc-Lys(Ac) for Fmoc-Thr(O-tBu) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Lys(Ac)-Nva-Ile-Arg-ProNHCH$_2$CH$_3$ as the trifluoracetate salt: $R_f$=4.328 minutes (gradient varying over 10 minutes from 20% to 80% acetonitrile/water containing 0.01% TFA); MS (ESI) m/e 723.5 (M+H)$^+$; Amino Acid Anal.: 1.20 Lys; 0.89 Nva; 1.02 Ile; 0.97 Arg; 1.00 Pro.

EXAMPLE 61

N-Ac-Gln-Nva-Ile-Arg-ProNHCH$_2$CH$_3$ (SEQ ID NO: 18)

The desired product was prepared by substituting Fmoc-Gln(Trt) for Fmoc-Thr(O-tBu) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Gln-Nva-Ile-Arg-ProNHCH$_2$CH$_3$ as the trifluoracetate salt: $R_f$=3.993 minutes (gradient varying over 10 minutes from 20% to 80% acetonitrile/water containing 0.01% TFA); MS (ESI) m/e 681.4 (M+H)$^+$; Amino Acid Anal.: 1.01 Glu; 0.90 Nva; 1.01 Ile; 0.97 Arg; 1.01 Pro.

EXAMPLE 62

N-Ac-alloThr-Ser-Ile-Arg-ProNHCH$_2$CH$_3$ (SEQ ID NO: 19)

The desired product was prepared by substituting Fmoc-alloThr(O-tBu) for Fmoc-Thr(O-tBu) and Fmoc-Ser(O-tBu) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-alloThr-Ser-Ile-Arg-ProNHCH$_2$CH$_3$ as the trifluoracetate salt: $R_f$=3.507 minutes (gradient varying over 10 minutes from 20% to 80% acetonitrile/water containing 0.01% TFA); MS (ESI) m/e 642.3 (M+H)$^+$; Amino Acid Anal.: 0.40 Thr; 0.09 Ser; 1.00 Ile; 0.96 Arg; 1.05 Pro.

EXAMPLE 63

N-Ac-Thr-Nva-Ile-Arg-D-ProNHCH$_2$CH$_3$

The desired product was prepared by substituting Fmoc-D-Pro-Sieber ethylamide resin for Fmoc-Pro-Sieber amide resin in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Nva-Ile-Arg-D-ProNHCH$_2$CH$_3$ as the trifluoracetate salt: $R_f$=4.232 minutes (gradient varying over 10 minutes from 20% to 80% acetonitrile/water containing 0.01% TFA); MS (ESI) m/e 654.3 (M+H)$^+$; Amino Acid Anal.: 0.39 Thr; 0.91 Nva; 1.01 Ile; 0.98 Arg; 1.01 Pro.

EXAMPLE 64

N-Ac-alloThr-Nva-Pro-Arg-ProNHCH$_2$CH$_3$ (SEQ ID NO:20)

The desired product was prepared by substituting Fmoc-alloThr(O-tBu) for Fmoc-Thr(O-tBu) and Fmoc-Pro for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-alloThr-Nva-Pro-Arg-ProNHCH$_2$CH$_3$ as the trifluoracetate salt: $R_f$=3.586 minutes (gradient varying over 10 minutes from 20% to 80% acetonitrile/water containing 0.01% TFA); MS (ESI) m/e 638.3 (M+H)$^+$; Amino Acid Anal.: 0.43 Thr; 0.88 Nva; 1.00 Arg; 2.00 Pro.

EXAMPLE 65

N-Ac-Trp-Nva-Ile-Arg-ProNHCH$_2$CH$_3$ (SEQ ID NO:21)

The desired product was prepared by substituting Fmoc-Trp(Boc) for Fmoc-Thr(O-tBu) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Trp-Nva-Ile-Arg-ProNHCH$_2$CH$_3$ as the trifluoracetate salt: R$_f$=5.861 minutes (gradient varying over 10 minutes from 20% to 80% acetonitrile/water containing 0.01% TFA); MS (ESI) m/e 739.5 (M+H)$^+$; Amino Acid Anal.: 0.22 Trp; 0.90 Nva; 0.95 Ile; 1.03 Arg; 1.03 Pro.

EXAMPLE 66

N-Ac-Thr-Nle-Ile-Arg-ProNHCH$_2$CH$_3$ (SEQ ID NO:22)

The desired product was prepared by substituting Fmoc-Nle for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Nle-Ile-Arg-ProNHCH$_2$CH$_3$ as the trifluoracetate salt: R$_f$=4.544 minutes (gradient varying over 10 minutes from 20% to 80% acetonitrile/water containing 0.01% TFA); MS (ESI) m/e 668.4 (M+H)$^+$; Amino Acid Anal.: 0.41 Thr; 1.01 Ile; 0.99 Arg; 1.00 Pro.

EXAMPLE 67

N-Ac-Thr-D-Nva-Ile-Arg-ProNHCH$_2$CH$_3$

The desired product was prepared by substituting Fmoc-D-Nva for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-D-Nva-Ile-Arg-ProNHCH$_2$CH$_3$ as the trifluoracetate salt: R$_f$=4.373 minutes (gradient varying over 10 minutes from 20% to 80% acetonitrile/water containing 0.01% TFA); MS (ESI) m/e 654.4 (M+H)$^+$; Amino Acid Anal.: 0.40 Thr; 0.89 Nva; 1.03 Ile; 0.98 Arg; 1.00 Pro.

EXAMPLE 68

N-Ac-Thr-Trp-Ile-Arg-Pro-D-AlaNH$_2$

The desired product was prepared by substituting Fmoc-D-Ala-Sieber amide for Fmoc-Pro-Sieber ethylamide and Fmoc-Trp(Boc) for Fmoc-Nva and adding a coupling with Fmoc-Pro before the coupling with Fmoc-Arg(Pmc) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Trp-Ile-Arg-Pro-D-AlaNH$_2$ as the trifluoracetate salt: R$_f$=4.927 minutes (gradient varying over 10 minutes from 20% to 80% acetonitrile/water containing 0.01% TFA); MS (ESI) m/e 784.5 (M+H)$^+$; Amino Acid Anal.: 0.39 Thr; 0.10 Trp; 1.04 Ile; 0.91 Arg; 1.03 Pro; 1.02 Ala.

EXAMPLE 69

N-Ac-Thr-Ser-Ile-Arg-Pro-D-AlaNH$_2$

The desired product was prepared by substituting Fmoc-D-Ala-Sieber amide resin for Fmoc-Pro-Sieber ethylamide resin and Fmoc-Ser(O-tBu) for Fmoc-Nva and adding a coupling with Fmoc-Pro before the coupling with Fmoc-Arg(Pmc) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Ser-Ile-Arg-Pro-D-AlaNH$_2$ as the trifluoracetate salt: R$_f$=3.322 minutes (gradient varying over 10 minutes from 20% to 80% acetonitrile/water containing 0.01% TFA); MS (ESI) m/e 685.4 (M+H)$^+$; Amino Acid Anal.: 0.37 Thr; 0.10 Ser; 1.01 Ile; 0.92 Arg; 1.07 Pro; 1.01 Ala.

EXAMPLE 70

N-Ac-Thr-D-Gln-Ile-Arg-ProNHCH$_2$CH$_3$

The desired product was prepared by substituting Fmoc-D-Gln(Trt) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-D-Gln-Ile-Arg-ProNHCH$_2$CH$_3$ as the trifluoracetate salt: R$_f$=3.292 minutes (gradient varying over 10 minutes from 20% to 80% acetonitrile/water containing 0.01% TFA); MS (ESI) m/e 683.4 (M+H)$^+$.

EXAMPLE 71

N-Ac-Ser-Ser-Ile-Arg-Pro-D-AlaNH$_2$

The desired product was prepared by substituting Fmoc-D-Ala-Sieber amide resin for Fmoc-Pro-Sieber ethyl amide resin, Fmoc-Ser(O-tBu) for both Fmoc-Thr(O-tBu) and Fmoc-Nva, and adding a coupling with Fmoc-Pro before the coupling with Fmoc-Arg(Pmc) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Ser-Ser-Ile-Arg-Pro-D-AlaNH$_2$ as the trifluoracetate salt: R$_f$=3.107 minutes (gradient varying over 10 minutes from 20% to 80% acetonitrile/water containing 0.01% TFA); MS (ESI) m/e 671.3 (M+H)$^+$.

EXAMPLE 72

N-Ac-Thr-Nva-Pro-Arg-ProNHCH$_2$CH$_3$ (SEQ ID NO:23)

The desired product was prepared by substituting Fmoc-Pro for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Nva-Pro-Arg-ProNHCH$_2$CH$_3$ as the trifluoracetate salt: R$_f$=3.654 minutes (gradient varying over 10 minutes from 20% to 80% acetonitrile/water containing 0.01% TFA); MS (ESI) m/e 638.4 (M+H)$^+$.

EXAMPLE 73

N-Ac-Ser-Gln-D-Ile-Arg-ProNHCH$_2$CH$_3$

The desired product was prepared by substituting Fmoc-Ser(O-tBu) for Fmoc-Thr(O-tBu), Fmoc-Gln(Trt) for Fmoc-Nva, and Fmoc-D-Ile for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Ser-Gln-D-Ile-Arg-ProNHCH$_2$CH$_3$ as the trifluoracetate salt: R$_t$=3.382 minutes (gradient varying over 10 minutes from 20% to 80% acetonitrile/water containing 0.01% TFA); MS (ESI) m/e 669.4 (M+H)$^+$.

EXAMPLE 74

N-Ac-Thr-Trp-D-Ile-Arg-ProNHCH$_2$CH$_3$

The desired product was prepared by substituting Fmoc-Trp(Boc) for Fmoc-Nva and Fmoc-D-Ile for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Trp-D-Ile-Arg-ProNHCH$_2$CH$_3$ as the trifluoracetate salt: R$_t$=5.422 minutes (gradient varying over 10 minutes from 20% to 80% acetonitrile/water containing 0.01% TFA); MS (ESI) m/e 741.5 (M+H)$^+$.

EXAMPLE 75

N-Ac-Ser-Gln-Lys(Ac)-Arg-ProNHCH$_2$CH$_3$ (SEQ ID NO:24)

The desired product was prepared by substituting Fmoc-Ser(O-tBu) for Fmoc-Thr(O-tBu), Fmoc-Gln(Trt) for Fmoc-Nva, and Fmoc-Lys(Ac) for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Ser-Gln-Lys(Ac)-Arg-ProNHCH$_2$CH$_3$ as the trifluoracetate salt: R$_t$=2.710 minutes (gradient varying over 10 minutes from 20% to 80% acetonitrile/water containing 0.01% TFA); MS (ESI) m/e 726.4 (M+H)$^+$.

EXAMPLE 76

N-Ac-Ser-Gln-Ile-Arg-Pro-D-AlaNH$_2$

The desired product was prepared by substituting Fmoc-D-Ala-Sieber amide resin for Fmoc-Pro-Sieber ethylamide resin, Fmoc-Ser(O-tBu) for Fmoc-Thr(O-tBu), Fmoc-Gln(Trt) for Fmoc-Nva, and adding a coupling with Fmoc-Pro before the coupling with Fmoc-Arg(Pmc) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Ser-Gln-Ile-Arg-Pro-D-AlaNH$_2$ as the trifluoracetate salt: R$_t$=3.004 minutes (gradient varying over 10 minutes from 20% to 80% acetonitrile/water containing 0.01% TFA); MS (ESI) m/e 712.4 (M+H)$^+$.

EXAMPLE 77

N-Ac-AllylGly-Gln-Ile-Arg-ProNHCH$_2$CH$_3$ (SEQ ID NO:25)

The desired product was prepared by substituting Fmoc-AllylGly for Fmoc-Thr(O-tBu) and Fmoc-Gln(Trt) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-AllylGly-Gln-Ile-Arg-ProNHCH$_2$CH$_3$ as the trifluoracetate salt: R$_t$=4.015 minutes (gradient varying over 10 minutes from 20% to 80% acetonitrile/water containing 0.01% TFA); MS (ESI) m/e 679.3 (M+H)$^+$.

EXAMPLE 78

N-Ac-Thr-Nva-Lys-Arg-ProNHCH$_2$CH$_3$ (SEQ ID NO:26)

The desired product was prepared by substituting Fmoc-Lys(Boc) for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Nva-Lys-Arg-ProNHCH$_2$CH$_3$ as the trifluoracetate salt: R$_t$=2.872 minutes (gradient varying over 10 minutes from 20% to 80% acetonitrile/water containing 0.01% TFA); MS (ESI) m/e 669.3 (M+H)$^+$.

EXAMPLE 79

N-Ac-Ser-D-Gln-Ile-Arg-ProNHCH$_2$CH$_3$

The desired product was prepared by substituting Fmoc-Ser(O-tBu) for Fmoc-Thr(O-tBu) and Fmoc-D-Gln(Trt) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Ser-D-Gln-Ile-Arg-ProNHCH$_2$CH$_3$ as the trifluoracetate salt: R$_t$=3.276 minutes (gradient varying over 10 minutes from 20% to 80% acetonitrile/water containing 0.01% TFA); MS (ESI) m/e 669.3 (M+H)$^+$.

EXAMPLE 80

N-Ac-D-Ile-Thr-Arg-Ile-Arg-NHCH$_2$CH$_3$

The desired product was prepared by substituting Fmoc-Arg(Pmc) for Fmoc-Nva and omitting the Fmoc-Pro coupling in Example 1. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-Ile-Thr-Arg-Ile-Arg-NHCH$_2$CH$_3$ as the trifluoroacetate salt: R$_t$=1.05 minutes (gradient varying over 10 minutes from 20% to 80% acetonitrile/water containing 0.01% TFA); MS (ESI) m/e 727.4 (M+H)$^+$; Amino Acid Anal.: 2.01 Ile; 0.56 Thr; 2.31 Arg.

EXAMPLE 81

N-Ac-D-aIle-Ser-Ser-Lys(Ac)-Arg-ProNHCH$_2$CH$_3$

The desired product was prepared by substituting Fmoc-D-aIle for Fmoc-D-Ile, Fmoc-Ser(O-tBu) for Fmoc-Thr(O-tBu) and Fmoc-Nva, and Fmoc-Lys(Ac) for Fmoc-Ile in Example 1 After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-aIle-Ser-Ser-Lys(Ac)-Arg-ProNHCH$_2$CH$_3$ as the trifluoroacetate salt: $R_t$=3.671 minutes (gradient varying over 10 minutes from 20% to 80% acetonitrile/water containing 0.01% TFA); MS (ESI) m/e 798.7 (M+H)$^+$; Amino Acid Anal.: 0.19 Ser; 0.92 Ile; 0.98 Lys; 0.74 Arg; 1.0 Pro.

EXAMPLE 82

N-Ac-D-aIle-Ser-Ser-Nle-Arg-ProNHCH$_2$CH$_3$

The desired product was prepared by substituting Fmoc-D-aIle for Fmoc-D-Ile, Fmoc-Ser(O-tBu) for Fmoc-Thr(O-tBu) and Fmoc-Nva, and Fmoc-Nle for Fmoc-Ile in Example 1. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-aIle-Ser-Ser-Nle-Arg-ProNHCH$_2$CH$_3$ as the trifluoroacetate salt: $R_t$=4.394 minutes (gradient varying over 10 minutes from 20% to 80% acetonitrile/water containing 0.01% TFA); MS (ESI) m/e 741.6 (M+H)$^+$; Amino Acid Anal.: 0.34 Ser; 0.99 Ile; 0.96 Nle; 0.99 Arg; 1.05 Pro.

EXAMPLE 83

N-Ac-D-aIle-Ser-Ser-Pro-Arg-ProNHCH$_2$CH$_3$

The desired product was prepared by substituting Fmoc-D-aIle for Fmoc-D-Ile, Fmoc-Ser(O-tBu) for Fmoc-Thr(O-tBu) and Fmoc-Nva, and Fmoc-Pro for Fmoc-Ile in Example 1. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-aIle-Ser-Ser-Pro-Arg-ProNHCH$_2$CH$_3$ as the trifluoroacetate salt: $R_t$=3.37 minutes (gradient varying over 10 minutes from 20% to 80% acetonitrile/water containing 0.01% TFA); MS (ESI) m/e 725.5 (M+H)$^+$; Amino Acid Anal.: 0.18 Ser; 1.00 Ile; 0.87 Arg; 2.13 Pro.

EXAMPLE 84

N-Ac-D-aIle-Ser-Ser-Nva-Arg-ProNHCH$_2$CH$_3$

The desired product was prepared by substituting Fmoc-D-aIle for Fmoc-D-Ile, Fmoc-Ser(O-tBu) for Fmoc-Thr(O-tBu) and Fmoc-Nva, and Fmoc-Nva for Fmoc-Ile in Example 1. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-aIle-Ser-Ser-Nva-Arg-ProNHCH$_2$CH$_3$ as the trifluoroacetate salt: $R_t$=3.938 minutes (gradient varying over 10 minutes from 20% to 80% acetonitrile/water containing 0.01% TFA); MS (ESI) m/e 727.5 (M+H)$^+$; Amino Acid Anal.: 0.30 Ser; 1.03 Nva; 1.04 Ile; 0.94 Arg; 1.03 Pro.

EXAMPLE 85

N-Ac-D-Ile-Thr-Nva-Ile-Arg-NHCH$_2$CH$_3$

The desired product was prepared by omitting the coupling with Fmoc-Pro in Example 1. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-Ile-Thr-Nva-Ile-Arg-NHCH$_2$CH$_3$ as the trifluoroacetate salt: $R_t$=2.15 minutes (gradient varying over 10 minutes from 20% to 80% acetonitrile/water containing 0.01% TFA); MS (ESI) m/e 670.3 (M+H)$^+$; Amino Acid Anal.: 0.55 Thr; 1.02 Nva; 2.02 Ile; 1.21 Arg.

EXAMPLE 86

N-Ac-D-aIle-Ser-Ser-Lys-Arg-ProNHCH$_2$CH$_3$

The desired product was prepared by substituting Fmoc-D-aIle for Fmoc-D-Ile, Fmoc-Ser(O-tBu) for Fmoc-Thr(O-tBu) and Fmoc-Nva, and Fmoc-Lys(Boc) for Fmoc-Ile in Example 1. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-aIle-Ser-Ser-Lys-Arg-ProNHCH$_2$CH$_3$ as the trifluoroacetate salt: $R_t$=3.272 minutes (gradient varying over 10 minutes from 20% to 80% acetonitrile/water containing 0.01% TFA); MS (ESI) m/e 756.5 (M+H)$^+$.

EXAMPLE 87

N-Ac-D-aIle-Ser-Ser-Ile-Arg-ProNHCH(CH$_3$)$_2$

The desired product was prepared by substituting Fmoc-D-aIle for Fmoc-D-Ile, Fmoc-Pro-[4-(4-N-isopropylamino)methyl-3-methoxyphenoxy]butyryl AM resin for Fmoc-Pro Sieber ethylamide resin, and Fmoc-Ser(O-tBu) for Fmoc-Thr(O-tBu) and Fmoc-Nva in Example 1. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-aIle-Ser-Ser-Ile-Arg-ProNHCH(CH$_3$)$_2$ as the trifluoroacetate salt: $R_t$=3.04 minutes (gradient varying over 10 minutes from 20% to 80% acetonitrile/water containing 0.01% TFA); MS (ESI) m/e 755.5 (M+H)$^+$.

EXAMPLE 88

N-Ac-D-aIle-Ser-Ser-Gln-Arg-ProNHCH$_2$CH$_3$

The desired product was prepared by substituting Fmoc-D-aIle for Fmoc-D-Ile, Fmoc-Ser(O-tBu) for Fmoc-Thr(O-tBu) and Fmoc-Nva, and Fmoc-Gln(Trt) for Fmoc-Ile in Example 1. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-aIle-Ser-Ser-Gln-Arg-ProNHCH$_2$CH$_3$ as the trifluoroacetate salt: R$_t$=3.039 minutes (gradient varying over 10 minutes from 20% to 80% acetonitrile/water containing 0.01% TFA); MS (ESI) m/e 756.5 (M+H)$^+$.

EXAMPLE 89

N-Ac-D-aIle-Ser-Ser-Cit-Arg-ProNHCH$_2$CH$_3$

The desired product was prepared by substituting Fmoc-D-aIle for Fmoc-D-Ile, Fmoc-Ser(O-tBu) for Fmoc-Thr(O-tBu) and Fmoc-Nva, and Fmoc-Cit for Fmoc-Ile in Example 1. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-aIle-Ser-Ser-Cit-Arg-Pro-NHCH$_2$CH$_3$ as the trifluoroacetate salt: R$_t$=2.796 minutes (gradient varying over 10 minutes from 20% to 80% acetonitrile/water containing 0.01% TFA); MS (ESI) m/e 785.5 (M+H)$^+$.

EXAMPLE 90

N-Ac-D-Ile-Met-Gln-Ile-Arg-ProNHCH$_2$CH$_3$

The desired product was prepared by substituting Fmoc-Met for Fmoc-Thr(O-tBu) and Fmoc-Gln(Trt) for Fmoc-Nva in Example 1. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-Ile-Met-Gln-Ile-Arg-ProNHCH$_2$CH$_3$ as the trifluoroacetate salt: R$_t$=4.49 minutes (gradient varying over 10 minutes from 20% to 80% acetonitrile/water containing 0.01% TFA); MS (ESI) m/e 826.5 (M+H)$^+$.

EXAMPLE 91

N-Ac-Thr-Nva-D-Lys(Ac)-Arg-ProNHCH$_2$CH$_3$

The desired product was prepared by substituting Fmoc-D-Lys(Ac) for Fmoc-Ile in Example 43 After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Nva-D-Lys(Ac)-Arg-ProNHCH$_2$CH$_3$ as the trifluoroacetate salt: R$_t$=0.81 minutes (gradient varying over 10 minutes from 20% to 80% acetonitrile/water containing 0.01% TFA); MS (ESI) m/e 711.5 (M+H)$^+$.

EXAMPLE 92

N-Ac-Thr-Nva-Ile-Orn-ProNHCH$_2$CH$_3$ (SEQ ID NO:27)

The desired product was prepared by substituting Fmoc-Orn(Boc) for Fmoc-Arg(Pmc) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Nva-Ile-Orn-ProNHCH$_2$CH$_3$ as the trifluoroacetate salt: R$_t$=3.494 minutes (gradient varying over 10 minutes from 20% to 80% acetonitrile/water containing 0.01% TFA); MS (ESI) m/e 612.4 (M+H)$^+$; Amino Acid Anal.: 0.525 Thr; 1.007 Nva; 1.01 Ile; 1.013 Orn; 0.99 Pro.

EXAMPLE 93

N-Ac-Glu-Nva-Ile-Arg-ProNHCH$_2$CH$_3$ (SEQ ID NO:28)

The desired product was prepared by substituting Fmoc-Glu(O-tBu) for Fmoc-Thr(O-tBu) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Glu-Nva-Ile-Arg-ProNHCH$_2$CH$_3$ as the trifluoroacetate salt: R$_t$=3.676 minutes (gradient varying over 10 minutes from 20% to 80% acetonitrile/water containing 0.01% TFA); MS (ESI) m/c 682.4 (M+H)$^+$; Amino Acid Anal.: 1.014 Glu; 1.003 Nva; 1.007 Ile; 0.964 Arg; 1.015 Pro.

EXAMPLE 94

N-Ac-Asn-Nva-Ile-Arg-ProNHCH$_2$CH$_3$ (SEQ ID NO:29)

The desired product was prepared by substituting Fmoc-Asn(Trt) for Fmoc-Thr(O-tBu) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Asn-Nva-Ile-Arg-ProNHCH$_2$CH$_3$ as the trifluoroacetate salt: R$_t$=3.579 minutes (gradient varying over 10 minutes from 20% to 80% acetonitrile/water containing 0.01% TFA); MS (ESI) m/e 667.4 (M+H)$^+$; Amino Acid Anal.: 1.018 Asp; 1.052 Nva; 1.047 Ile; 0.998 Arg; 0.938 Pro.

EXAMPLE 95

N-Ac-Hser-Nva-Ile-Arg-ProNHCH$_2$CH$_3$ (SEQ ID NO:30)

The desired product was prepared by substituting Fmoc-Hser(Trt) for Fmoc-Thr(O-tBu) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Hser-Nva-Ile-Arg-ProNHCH$_2$CH$_3$ as the trifluoroacetate salt: R$_t$=1.35 minutes (gradient varying over 10 minutes from 20% to 80% acetonitrile/water containing 0.01% TFA); MS (ESI) m/e 654.5 (M+H)$^+$; Amino Acid Anal.: 1.35 Hser; 1.052 Nva; 1.002 Ile; 0.972 Arg; 1.026 Pro.

EXAMPLE 96

N-Ac-Sar-Nva-Ile-Arg-ProNHCH$_2$CH$_3$ (SEQ ID NO:31)

The desired product was prepared by substituting Fmoc-Sar for Fmoc-Thr(O-tBu) in Example 43. After workup the crude peptide was purified by HPLC using a C-18 column and a solvent system varying in gradient over 50 minutes from 5% to 100% acetonitrile/water containing 0.01% TFA.

The pure fractions were lyophilized to provide N-Ac-Sar-Nva-Ile-Arg-ProNHCH$_2$CH$_3$ as the trifluoroacetate salt: R$_t$=3.60 minutes (gradient varying over 10 minutes from 20% to 80% acetonitrile/water containing 0.01% TFA); MS (ESI) m/e 624.4 (M+H)$^+$; Amino Acid Anal.: 0.835 Sar; 1.035 Nva; 0.986 Ile; 0.980 Arg; 1.034 Pro.

EXAMPLE 97

N-Ac-Asp-Nva-Ile-Arg-ProNHCH$_2$CH$_3$ (SEQ ID NO:32)

The desired product was prepared by substituting Fmoc-Asp(O-tBu) for Fmoc-Thr(O-tBu) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Asp-Nva-Ile-Arg-ProNHCH$_2$CH$_3$ as the trifluoroacetate salt: R$_t$=3.622 minutes (gradient varying over 10 minutes from 20% to 80% acetonitrile/water containing 0.01% TFA); MS (ESI) m/e 668.4 (M+H)$^+$; Amino Acid Anal.: 1.036 Asp; 1.054 Nva; 1.045 Ile; 0.982 Arg; 0.937 Pro.

EXAMPLE 98

N-Ac-Ser-Gln-Nva-Arg-ProNHCH$_2$CH$_3$ (SEQ ID NO:33)

The desired product was prepared by substituting Fmoc-Ser(O-tBu) for Fmoc-Thr(O-tBu), Fmoc-Gln(Trt) for Fmoc-Nva, and Fmoc-Nva for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Ser-Gln-Nva-Arg-ProNHCH$_2$CH$_3$ as the trifluoroacetate salt: R$_t$=3.253 minutes (gradient varying over 10 minutes from 20% to 80% acetonitrile/water containing 0.01% TFA); MS (ESI) m/e 655.4 (M+H)$^+$; Amino Acid Anal.: 0.224 Ser; 1.046 Glu; 0.845 Nva; 0.969 Arg; 0.985 Pro.

EXAMPLE 99

N-Ac-Ser-Gln-Ile-Cit-ProNHCH$_2$CH$_3$ (SEQ ID NO:34)

The desired product was prepared by substituting Fmoc-Ser(O-tBu) for Fmoc-Thr(O-tBu), Fmoc-Gln(Trt) for Fmoc-Nva, and Fmoc-Cit for Fmoc-Arg(Pmc) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Ser-Gln-Ile-Cit-ProNHCH$_2$CH$_3$ as the trifluoroacetate salt: R$_t$=3.253 minutes (gradient varying over 10 minutes from 20% to 80% acetonitrile/water containing 0.01% TFA); MS (ESI) m/e 655.4 (M+H)$^+$; Amino Acid Anal.: 0.273 Ser; 1.012 Glu; 0.939 Ile; 1.043 Cit; 1.04 Pro.

EXAMPLE 100

N-Ac-Ser-Gln-Ile-3Pal-ProNHCH$_2$CH$_3$ (SEQ ID NO:35)

The desired product was prepared by substituting Fmoc-Ser(O-tBu) for Fmoc-Thr(O-tBu), Fmoc-Gln(Trt) for Fmoc-Nva, and Fmoc-3Pal for Fmoc-Arg(Pmc) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Ser-Gln-Ile-3Pal-ProNHCH$_2$CH$_3$ as the trifluoroacetate salt: R$_t$=4.031 minutes (gradient varying over 10 minutes from 20% to 80% acetonitrile/water containing 0.01% TFA); MS (ESI) m/e 661.3 (M+H)$^+$; Amino Acid Anal.: 0.23 Ser; 1.012 Glu; 1.025 Ile; 0.793 3Pal; 0.963 Pro.

EXAMPLE 101

N-Ac-Thr-Gln-Nva-Arg-ProNHCH$_2$CH$_3$ (SEQ ID NO:36)

The desired product was prepared by substituting Fmoc-Gln(Trt) for Fmoc-Nva and Fmoc-Nva for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Gln-Nva-Arg-ProNHCH$_2$CH$_3$ as the trifluoroacetate salt: R$_t$=3.4 minutes (gradient varying over 10 minutes from 20% to 80% acetonitrile/water containing 0.01% TFA); MS (ESI) m/e 669.4 (M+H)$^+$; Amino Acid Anal.: 0.535 Thr; 1.023 Glu; 1.09 Nva; 1.013 Arg; 0.964 Pro.

EXAMPLE 102

N-Ac-Thr-Asn-Ile-Arg-ProNHCH$_2$CH$_3$ (SEQ ID NO:37)

The desired product was prepared by substituting Fmoc-Asn(Trt) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Asn-Ile-Arg-ProNHCH$_2$CH$_3$ as the trifluoroacetate salt: R$_t$=3.4 minutes (gradient varying over 10 minutes from 20% to 80% acetonitrile/water containing 0.01% TFA); MS (ESI) m/e 669.4 (M+H)$^+$; Amino Acid Anal.: 0.591 Thr; 1.02 Asp; 1.003 Ile; 1.005 Arg; 0.972 Pro.

EXAMPLE 103

N-Ac-Thr-D-Asn-Ile-Arg-ProNHCH$_2$CH$_3$

The desired product was prepared by substituting Fmoc-D-Asn(Trt) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-D-Asn-Ile-Arg-ProNHCH$_2$CH$_3$ as the trifluoroacetate salt: R$_t$=3.615 minutes (gradient varying over 10 minutes from 20% to 80% acetonitrile/water containing 0.01% TFA); MS (ESI) m/e 669.4 (M+H)$^+$; Amino Acid Anal.: 0.62 Thr; 0.908 Asp; 0.995 Ile; 1.044 Arg; 1.053 Pro.

EXAMPLE 104

H-Thr-Nva-Pro-Arg-ProNHCH$_2$CH$_3$ (SEQ ID NO:38)

The desired product was prepared by substituting Fmoc-Pro for Fmoc-Ile and omitting the last acetylation step in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide H-Thr-Nva-Pro-Arg-ProNHCH$_2$CH$_3$ as the trifluoroacetate salt: R$_t$=3.30 minutes (gradient varying over 10 minutes from 20% to 80% acetonitrile/water containing 0.01% TFA); MS (ESI) m/e 596.4 (M+H)$^+$; Amino Acid Anal.: 0.604 Thr; 1.20 Nva; 0.955 Arg; 2.045 Pro.

EXAMPLE 105

N-Ac-D-Thr-Nva-Pro-Arg-ProNHCH$_2$CH$_3$

The desired product was prepared by substituting Fmoc-D-Thr(O-tBu) for Fmoc-Thr(O-tBu) and Fmoc-Pro for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-Thr-Nva-Pro-Arg-ProNHCH$_2$CH$_3$ as the trifluoroacetate salt: R$_t$=3.82 minutes (gradient varying over 10 minutes from 20% to 80% acetonitrile/water containing 0.01% TFA); MS (ESI) m/e 638.5 (M+H)$^+$; Amino Acid Anal.: 0.568 Thr; 1.17 Nva; 0.997 Arg; 2.003 Pro.

EXAMPLE 106

N-Ac-Thr-Nva-D-Pro-Arg-ProNHCH$_2$CH$_3$

The desired product was prepared by substituting Fmoc-D-Pro for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Nva-D-Pro-Arg-ProNHCH$_2$CH$_3$ as the trifluoroacetate salt: R$_t$=3.45 minutes (gradient varying over 10 minutes from 20% to 80% acetonitrile/water containing 0.01% TFA); MS (ESI) m/e 638.4 (M+H)$^+$; Amino Acid Anal.: 0.614 Thr; 1.195 Nva; 1.073 Arg; 1.927 Pro.

EXAMPLE 107

N-Ac-Nva-Gln-Ile-Arg-ProNHCH$_2$CH$_3$ (SEQ ID NO:39)

The desired product was prepared by substituting Fmoc-Nva for Fmoc-Thr(O-tBu) and Fmoc-Gln(Trt) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Nva-Gln-Ile-Arg-ProNHCH$_2$CH$_3$ as the trifluoroacetate salt: R$_t$=3.822 minutes (gradient varying over 10 minutes from 20% to 80% acetonitrile/water containing 0.01% TFA); MS (ESI) m/e 681.5.

EXAMPLE 108

N-Ac-D-Nva-Pro-Ile-Arg-ProNHCH$_2$CH$_3$

The desired product was prepared by substituting Fmoc-D-Nva for Fmoc-Thr(O-tBu) and Fmoc-Pro for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-Nva-Pro-Ile-Arg-ProNHCH$_2$CH$_3$ as the trifluoroacetate salt: R$_t$=5.008 minutes (gradient varying over 10 minutes from 20% to 80% acetonitrile/water containing 0.01% TFA); MS (ESI) m/e 638.4.

EXAMPLE 109

N-Ac-Thr-Arg-Ile-Cit-ProNHCH$_2$CH$_3$ (SEQ ID NO:40)

The desired product was prepared by substituting Fmoc-Arg(Pmc) for Fmoc-Nva and Fmoc-Cit for Fmoc-Arg(Pmc) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Arg-Ile-Cit-ProNHCH$_2$CH$_3$ as the trifluoroacetate salt: R$_t$=2.868 minutes (gradient varying over 10 minutes from 20% to 80% acetonitrile/water containing 0.01% TFA); MS (ESI) m/e 712.5.

EXAMPLE 110

N-Ac-Thr-Gln-Lys(Ac)-Arg-ProNHCH$_2$CH$_3$ (SEQ ID NO:41)

The desired product was prepared by substituting Fmoc-Gln(Trt) for Fmoc-Nva and Fmoc-Lys(Ac) for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Gln-Lys(Ac)-Arg-ProNHCH$_2$CH$_3$ as the trifluoroacetate salt: R$_t$=2.334 minutes (gradient varying over 10 minutes from 20% to 80% acetonitrile/water containing 0.01% TFA); MS (ESI) m/e 740.5.

EXAMPLE 111

N-Ac-Thr-Nva-Pro-Arg-Pro-D-AlaNH$_2$

The desired product was prepared by substituting Fmoc-D-Ala-Sieber amide resin for Fmoc-Pro-Sieber ethylamide resin, adding a coupling with Fmoc-Pro before the coupling with Fmoc-Arg(Pmc), and substituting Fmoc-Pro for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Nva-Pro-Arg-Pro-D-AlaNH$_2$ as the trifluoroacetate salt: R$_t$=2.943 minutes (gradient varying over 10 minutes from 20% to 80% acetonitrile/water containing 0.01% TFA); MS (ESI) m/e 681.5.

EXAMPLE 112

N-Ac-Thr-Ser-Lys(Ac)-Arg-ProNHCH$_2$CH$_3$ (SEQ ID NO:42)

The desired product was prepared by substituting Fmoc-Ser(O-tBu) for Fmoc-Nva and Fmoc-Lys(Ac) for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Ser-Lys(Ac)-Arg-ProNHCH$_2$CH$_3$ as the trifluoroacetate salt: $R_t$=2.428 minutes (gradient varying over 10 minutes from 20% to 80% acetonitrile/water containing 0.01% TFA); MS (ESI) m/e 699.5.

EXAMPLE 113

N-Ac-Thr-Ser-Pro-Arg-Pro-D-AlaNH$_2$

The desired product was prepared by substituting Fmoc-D-Ala-Sieber amide resin for Fmoc-Pro-Sieber ethylamide resin, adding a coupling with Fmoc-Pro before the coupling with Fmoc-Arg(Pmc), and substituting Fmoc-Ser(O-tBu) for Fmoc-Nva and Fmoc-Pro for Fmoc-Ile in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Ser-Pro-Arg-Pro-D-AlaNH$_2$ as the trifluoroacetate salt: $R_t$=2.028 minutes (gradient varying over 10 minutes from 20% to 80% acetonitrile/water containing 0.01% TFA); MS (ESI) m/e 669.3.

EXAMPLE 114

N-Ac-Thr-Cit-Ile-Arg-ProNHCH$_2$CH$_3$ (SEQ ID NO:43)

The desired product was prepared by substituting Fmoc-Cit for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Cit-Ile-Arg-ProNHCH$_2$CH$_3$ as the trifluoroacetate salt: $R_t$=2.839 minutes (gradient varying over 10 minutes from 20% to 80% acetonitrile/water containing 0.01% TFA); MS (ESI) m/e 712.5.

EXAMPLE 115

N-(3-Methylvaleryl)-Thr-Gln-Ile-Arg-ProNHCH$_2$CH$_3$ (SEQ ID NO:44)

The desired product was prepared by substituting Fmoc-Gln(Trt) for Fmoc-Nva and 3-methylvaleric acid for acetic acid in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-(3-methylvaleryl)-Thr-Gln-Ile-Arg-ProNHCH$_2$CH$_3$ as the trifluoroacetate salt: $R_t$=4.501 minutes (gradient varying over 10 minutes from 20% to 80% acetonitrile/water containing 0.01% TFA); MS (ESI) m/e 739.5.

EXAMPLE 116

N-(3-Methylvaleryl)-Thr-Nva-Ile-Arg-ProNHCH$_2$CH$_3$ (SEQ ID NO:45)

The desired product was prepared by substituting 3-methylvaleric acid for acetic acid in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-(3-methylvaleryl)-Thr-Nva-Ile-Arg-ProNHCH$_2$CH$_3$ as the trifluoroacetate salt: $R_t$=4.82 minutes (gradient varying over 10 minutes from 20% to 80% acetonitrile/water containing 0.01% TFA); MS (ESI) m/e 710.5.

EXAMPLE 117

N-Ac-Ser-Trp-Ile-Arg-ProNHCH$_2$CH$_3$ (SEQ ID NO:46)

The desired product was prepared by substituting Fmoc-Ser(O-tBu) for Fmoc-Thr(O-tBu) and Fmoc-Trp(Boc) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Ser-Trp-Ile-Arg-ProNHCH$_2$CH$_3$ as the trifluoroacetate salt: $R_t$=4.539 minutes (gradient varying over 10 minutes from 20% to 80% acetonitrile/water containing 0.01% TFA); MS (ESI) m/e 727.4.

EXAMPLE 118

N-Ac-Thr-Trp-Ile-Arg-ProNHCH$_2$CH$_3$ (SEQ ID NO:47)

The desired product was prepared by substituting Fmoc-Trp(Boc) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Trp-Ile-Arg-ProNHCH$_2$CH$_3$ as the trifluoroacetate salt: $R_t$=4.589 minutes (gradient varying over 10 minutes from 20% to 80% acetonitrile/water containing 0.01% TFA); MS (ESI) m/e 741.5.

EXAMPLE 119

N-Ac-D-Nva-Gln-Ile-Arg-ProNHCH$_2$CH$_3$

The desired product was prepared by substituting Fmoc-D-Nva for Fmoc-Thr(O-tBu) and Fmoc-Gln(Trt) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-Nva-Gln-Ile-Arg-ProNHCH$_2$CH$_3$ as the trifluoroacetate salt: $R_t$=3.692 minutes (gradient varying over 10 minutes from 20% to 80% acetonitrile/water containing 0.01% TFA); MS (ESI) m/e 681.4.

EXAMPLE 120

N-Ac-Thr-Lys(Ac)-Ile-Arg-ProNHCH$_2$CH$_3$ (SEQ ID NO:48)

The desired product was prepared by substituting Fmoc-Lys(Ac) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Lys(Ac)-Ile-Arg-ProNHCH$_2$CH$_3$ as the trifluoroacetate salt: R$_t$=3.311 minutes (gradient varying over 10 minutes from 20% to 80% acetonitrile/water containing 0.01% TFA); MS (ESI) m/e 725.5.

EXAMPLE 121

N-Ac-bAla-Thr-Nva-Ile-Arg-ProNHCH$_2$CH$_3$ (SEQ ID NO:49)

The desired product was prepared by coupling with Fmoc-β-alanine before the coupling with acetic acid in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-bAla-Thr-Nva-Ile-Arg-ProNHCH$_2$CH$_3$ as the trifluoroacetate salt: R$_t$=3.625 minutes (gradient varying over 10 minutes from 20% to 80% acetonitrile/water containing 0.01% TFA); MS (ESI) m/e 725.5.

EXAMPLE 122

N-Ac-bAla-Thr-Gln-Ile-Arg-ProNHCH$_2$CH$_3$ (SEQ ID NO:50)

The desired product was prepared by substituting Fmoc-Gln(Trt) for Fmoc-Nva and coupling with Fmoc-β-alanine before the coupling with acetic acid in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-bAla-Thr-Gln-Ile-Arg-ProNHCH$_2$CH$_3$ as the trifluoroacetate salt: R$_t$=2.844 minutes (gradient varying over 10 minutes from 20% to 80% acetonitrile/water containing 0.01% TFA); MS (ESI) m/e 754.5.

EXAMPLE 123

N-Ac-Ser-D-Gln-Ile-Arg-ProNHCH$_2$CH$_3$

The desired product was prepared by substituting Fmoc-Ser(O-tBu) for Fmoc-Thr(O-tBu) and Fmoc-D-Gln(Trt) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Ser-D-Gln-Ile-Arg-ProNHCH$_2$CH$_3$ as the trifluoroacetate salt: R$_t$=2.542 minutes (gradient varying over 10 minutes from 20% to 80% acetonitrile/water containing 0.01% TFA); MS (ESI) m/e 712.4.

EXAMPLE 124

N-Ac-D-Leu-Asp-Nva-Ile-Arg-ProNHCH$_2$CH$_3$

The desired product was prepared by substituting Fmoc-D-Leu for Fmoc-D-Ile and Fmoc-Asp(O-tBu) for Fmoc-Thr(O-tBu) in Example 1. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-Leu-Asp-Nva-Ile-Arg-ProNHCH$_2$CH$_3$ as the trifluoroacetate salt: R$_t$=1.86 minutes (gradient varying over 10 minutes from 20% to 80% acetonitrile/water containing 0.01% TFA); MS (ESI) m/e 781.6; Amino Acid Anal.: 1.01 Leu; 0.97 Asp; 1.00 Nva; 1.03 Ile; 1.10 Arg; 1.06 Pro.

EXAMPLE 125

N-Ac-D-Ile-Gln-Ile-Arg-ProNHCH$_2$CH$_3$

The desired product was prepared by substituting Fmoc-D-Ile for Fmoc-Thr(O-tBu) and Fmoc-Gln(Trt) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-Ile-Gln-Ile-Arg-ProNHCH$_2$CH$_3$ as the trifluoroacetate salt: R$_t$=3.73 minutes (gradient varying over 10 minutes from 20% to 80% acetonitrile/water containing 0.01% TFA); MS (ESI) m/e 695.4.

EXAMPLE 126

N-Ac-D-Ala-Gln-Ile-Arg-ProNHCH$_2$CH$_3$

The desired product was prepared by substituting Fmoc-D-Ala for Fmoc-Thr(O-tBu) and Fmoc-Gln(Trt) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-Ala-Gln-Ile-Arg-ProNHCH$_2$CH$_3$ as the trifluoroacetate salt: R$_t$=2.981 minutes (gradient varying over 10 minutes from 20% to 80% acetonitrile/water containing 0.01% TFA); MS (ESI) m/e 653.4.

EXAMPLE 127

N-Ac-D-Thr-Gln-Ile-Arg-ProNHCH$_2$CH$_3$

The desired product was prepared by substituting Fmoc-D-Thr(O-tBu) for Fmoc-Thr(O-tBu) and Fmoc-Gln(Trt) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-Thr-Gln-Ile-Arg-ProNHCH$_2$CH$_3$ as the trifluoroacetate salt: R$_t$=2.927 minutes (gradient varying over 10 minutes from 20% to 80% acetonitrile/water containing 0.01% TFA); MS (ESI) m/e 683.4.

EXAMPLE 128

N-Ac-D-Ser-Gln-Ile-Arg-ProNHCH$_2$CH$_3$

The desired product was prepared by substituting Fmoc-D-Ser(O-tBu) for Fmoc-Thr(O-tBu) and Fmoc-Gln(Trt) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-Ser-Gln-Ile-Arg-ProNHCH$_2$CH$_3$ as the trifluoroacetate salt: R$_t$=2.763 minutes (gradient varying over 10 minutes from 20% to 80% acetonitrile/water containing 0.01% TFA); MS (ESI) m/e 669.3.

EXAMPLE 129

N-Ac-D-Pro-Gln-Ile-Arg-ProNHCH$_2$CH$_3$

The desired product was prepared by substituting Fmoc-D-Pro for Fmoc-Thr(O-tBu) and Fmoc-Gln(Trt) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-Pro-Gln-Ile-Arg-ProNHCH$_2$CH$_3$ as the trifluoroacetate salt: R$_t$=3.376 minutes (gradient varying over 10 minutes from 20% to 80% acetonitrile/water containing 0.01% TFA); MS (ESI) m/e 679.4.

EXAMPLE 130

N-Ac-D-aIle-Gln-Ile-Arg-ProNHCH$_2$CH$_3$

The desired product was prepared by substituting Fmoc-D-aIle for Fmoc-Thr(O-tBu) and Fmoc-Gln(Trt) for Fmoc-Nva in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-D-aIle-Gln-Ile-Arg-ProNHCH$_2$CH$_3$ as the trifluoroacetate salt: R$_t$=3.778 minutes (gradient varying over 10 minutes from 20% to 80% acetonitrile/water containing 0.01% TFA); MS (ESI) m/e 695.4.

EXAMPLE 131

N-Ac-D-Nva-Asn-Ile-Arg-ProNHCH$_2$CH$_3$

The desired product can be prepared by substituting Fmoc-D-Nva for Fmoc-Thr(O-tBu) and Fmoc-Asn(Trt) for Fmoc-Nva in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Nva-Asn-Ile-Arg-ProNHCH$_2$CH$_3$ as the trifluoroacetate salt.

EXAMPLE 132

N-Ac-D-Nva-Arg-Ile-Arg-ProNHCH$_2$CH$_3$

The desired product can be prepared by substituting Fmoc-D-Nva for Fmoc-Thr(O-tBu) and Fmoc-Arg(Pmc) for Fmoc-Nva in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Nva-Arg-Ile-Arg-ProNHCH$_2$CH$_3$ as the trifluoroacetate salt.

EXAMPLE 133

N-Ac-D-Nva-Thr-Ile-Arg-ProNHCH$_2$CH$_3$

The desired product can be prepared by substituting Fmoc-D-Nva for Fmoc-Thr(O-tBu) and Fmoc-Thr(O-tBu) for Fmoc-Nva in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Nva-Thr-Ile-Arg-ProNHCH$_2$CH$_3$ as the trifluoroacetate salt.

EXAMPLE 134

N-Ac-D-Nva-Ser-Ile-Arg-ProNHCH$_2$CH$_3$

The desired product can be prepared by substituting Fmoc-D-Nva for Fmoc-Thr(O-tBu) and Fmoc-Ser(O-tBu) for Fmoc-Nva in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Nva-Ser-Ile-Arg-ProNHCH$_2$CH$_3$ as the trifluoroacetate salt.

EXAMPLE 135

N-Ac-D-Nva-Glu-Ile-Arg-ProNHCH$_2$CH$_3$

The desired product can be prepared by substituting Fmoc-D-Nva for Fmoc-Thr(O-tBu) and Fmoc-Glu(O-tBu) for Fmoc-Nva in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Nva-Glu-Ile-Arg-ProNHCH$_2$CH$_3$ as the trifluoroacetate salt.

EXAMPLE 136

N-Ac-D-Met-Gln-Ile-Arg-ProNHCH$_2$CH$_3$

The desired product can be prepared by substituting Fmoc-D-Met for Fmoc-Thr(O-tBu) and Fmoc-Gln(Trt) for Fmoc-Nva in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Met-Gln-Ile-Arg-ProNHCH$_2$CH$_3$ as the trifluoroacetate salt.

EXAMPLE 137

N-Ac-D-Hser-Gln-Ile-Arg-ProNHCH$_2$CH$_3$

The desired product can be prepared by substituting Fmoc-D-Hser(Trt) for Fmoc-Thr(O-tBu) and Fmoc-Gln(Trt) for Fmoc-Nva in Example 43. After workup the crude peptide can be purified by HPLC using a C-18 column and

EXAMPLE 138

N-Ac-D-Nva-Lys(Nic)-Ile-Arg-ProNHCH$_2$CH$_3$

The desired product can be prepared by substituting Fmoc-D-Nva for Fmoc-Thr(O-tBu) and Fmoc-Lys(Nic) for Fmoc-Nva in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Nva-Lys(Nic)-Ile-Arg-ProNHCH$_2$CH$_3$ as the trifluoroacetate salt.

EXAMPLE 139

N-Ac-D-Nva-Gln-Lys(Ac)-Arg-ProNHCH$_2$CH$_3$

The desired product can be prepared by substituting Fmoc-D-Nva for Fmoc-Thr(O-tBu), Fmoc-Gln(Trt) for Fmoc-Nva, and Fmoc-Lys(Ac) for Fmoc-Ile in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Nva-Gln-Lys(Ac)-Arg-ProNHE as the trifluoroacetate salt.

EXAMPLE 140

N-Ac-D-Nva-Gln-Ile-Arg-Pro-D-AlaNH$_2$

The desired product can be prepared by substituting Fmoc-D-Ala-Sieber amide resin for Fmoc-Pro-Sieber ethylamide resin, adding a coupling with Fmoc-Pro before the coupling with Fmoc-Arg(Pmc), and substituting Fmoc-D-Nva for Fmoc-Thr(O-tBu) and Fmoc-Gln(Trt) for Fmoc-Nva in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Nva-Gln-Ile-Arg-Pro-D-AlaNH$_2$ as the trifluoroacetate salt.

EXAMPLE 141

N-Ac-D-Nva-Gln-Ile-Cit-ProNHCH$_2$CH$_3$

The desired product can be prepared by substituting Fmoc-D-Nva for Fmoc-Thr(O-tBu), Fmoc-Gln(Trt) for Fmoc-Nva, and Fmoc-Cit for Fmoc-Arg(Pmc) in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Nva-Gln-Ile-Cit-ProNHCH$_2$CH$_3$ as the trifluoroacetate salt.

EXAMPLE 142

N-Ac-D-Nva-Gln-Pro-Arg-ProNHCH$_2$CH$_3$

The desired product can be prepared by substituting Fmoc-D-Nva for Fmoc-Thr(O-tBu), Fmoc-Gln(Trt) for Fmoc-Nva, and Fmoc-Pro for Fmoc-Ile in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Nva-Gln-Pro-Arg-ProNHE as the trifluoroacetate salt.

EXAMPLE 143

N-Ac-D-Nva-Gln-Ile-Lys(Isp)-ProNHCH$_2$CH$_3$

The desired product can be prepared by substituting Fmoc-D-Nva for Fmoc-Thr(O-tBu), Fmoc-Gln(Trt) for Fmoc-Nva, and Fmoc-Lys(Isp) for Fmoc-Arg(Pmc) in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Nva-Gln-Ile-Lys(Isp)-ProNHCH$_2$CH$_3$ as the trifluoroacetate salt.

EXAMPLE 144

N-Ac-D-Nle-Gln-Ile-Arg-ProNHCH$_2$CH$_3$

The desired product can be prepared by substituting Fmoc-D-Nle for Fmoc-Thr(O-tBu) and Fmoc-Gln(Trt) for Fmoc-Nva in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Nle-Gln-Ile-Arg-ProNHCH$_2$CH$_3$ as the trifluoroacetate salt.

EXAMPLE 145

N-Ac-Nle-Gln-Ile-Arg-ProNHCH$_2$CH$_3$ (SEQ ID NO:51)

The desired product can be prepared by substituting Fmoc-Nle for Fmoc-Thr(O-tBu) and Fmoc-Gln(Trt) for Fmoc-Nva in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-Nle-Gln-Ile-Arg-ProNHCH$_2$CH$_3$ as the trifluoroacetate salt.

EXAMPLE 146

N-Ac-D-Nva-Gln-Ile-Arg-ProNHCH(CH$_3$)$_2$

The desired product can be prepared by substituting Fmoc-D-Nva for Fmoc-Thr(O-tBu), Fmoc-Gln(Trt) for Fmoc-Nva, and Fmoc-Pro-[4-(4-N-isopropylamino)methyl-3-methoxyphenoxy]butyryl AM resin for Fmoc-Pro Sieber ethylamide resin in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Nva-Gln-Ile-Arg-ProNHIsp as the trifluoroacetate salt.

(continued from previous page: a solvent system varying in gradient over 50 minutes from 5% to 100% acetonitrile/water containing 0.01% TFA. The pure fractions can be lyophilized to provide N-Ac-D-Hser-Gln-Ile-Arg-ProNHCH$_2$CH$_3$ as the trifluoroacetate salt.)

EXAMPLE 147

N-(6MeNic)-D-Nva-Gln-Ile-Arg-ProNHCH$_2$CH$_3$

The desired product can be prepared by substituting Fmoc-D-Nva for Fmoc-Thr(O-tBu), Fmoc-Gln(Trt) for Fmoc-Nva, and 6-methylnicotinic acid for acetic acid in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-(6MeNic)-D-Nva-Gln-Ile-Arg-ProNHCH$_2$CH$_3$ as the trifluoroacetate salt.

EXAMPLE 148

N-Ac-Nva-D-Gln-Ile-Arg-ProNHCH$_2$CH$_3$

The desired product can be prepared by substituting Fmoc-Nva for Fmoc-Thr(O-tBu) and Fmoc-D-Gln(Trt) for Fmoc-Nva in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-Nva-D-Gln-Ile-Arg-ProNHCH$_2$CH$_3$ as the trifluoroacetate salt.

EXAMPLE 149

N-Ac-Nva-D-Asn-Ile-Arg-ProNHCH$_2$CH$_3$

The desired product can be prepared by substituting Fmoc-Nva for Fmoc-Thr(O-tBu) and Fmoc-D-Asn(Trt) for Fmoc-Nva in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-Nva-D-Asn-Ile-Arg-ProNHCH$_2$CH$_3$ as the trifluoroacetate salt.

EXAMPLE 150

N-Ac-Nva-D-Ser-Ile-Arg-ProNHCH$_2$CH$_3$

The desired product can be prepared by substituting Fmoc-Nva for Fmoc-Thr(O-tBu) and Fmoc-D-Ser(O-tBu) for Fmoc-Nva in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-Nva-D-Ser-Ile-Arg-ProNHCH$_2$CH$_3$ as the trifluoroacetate salt.

EXAMPLE 151

N-Ac-Nva-D-Leu-Ile-Arg-ProNHCH$_2$CH$_3$

The desired product can be prepared by substituting Fmoc-Nva for Fmoc-Thr(O-tBu) and Fmoc-D-Leu for Fmoc-Nva in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-Nva-D-Leu-Ile-Arg-ProNHCH$_2$CH$_3$ as the trifluoroacetate salt.

EXAMPLE 152

N-Ac-Sar-Gly-Val-D-a le-Thr-OH

In the reaction vessel of a Rainin peptide synthesizer was placed H-Thr(O-tBu)-2-Chlorotrityl resin (0.2 g, 0.52 mMol/g loading). The resin was solvated with DMF and amino acids were coupled sequentially according to the following synthetic cycle:
(1) 3×1.5 minute washes with DMF;
(2) 2×15 minute deprotections using 20% piperidine;
(3) 6×3 minute washes with DMF;
(4) addition of amino acid;
(5) activation of amino acid with 0.4 M HBTU/NMM and coupling;
(6) 3×1.5 minute washes with DMF.

The protected amino acids were coupled to the resin in the following order:

| Protected Amino Acid | Coupling time |
| --- | --- |
| Fmoc-D-aIle | 30 minutes |
| Fmoc-Val | 30 minutes |
| Fmoc-Gly | 30 minutes |
| Fmoc-Sar | 30 minutes |
| Acetic acid | 30 minutes |

Upon completion of the synthesis the peptide was cleaved from the resin using a mixture of (95:2.5:2.5) TFA/anisole/water for 3 hours. The peptide solution was concentrated under vacuum and then precipitated with diethyl ether and collected by filtration. The crude peptide was purified by HPLC using a C-18 column and a solvent mixture varying over 50 minutes in a gradient from 5% to 100% acetonitrile/water containing 0.01% TFA. The pure fractions were lyophilized to provide N-Ac-Sar-Gly-Val-D-aIle-Thr-OH: $R_t$=0.60 minutes (gradient varying over 10 minutes from 20% to 80% acetonitrile/water containing 0.01% TFA); MS (ESI) m/e 502.28.

EXAMPLE 153

N-Ac-Thr-Gln-Ile-Arg-NHCH$_2$CH$_3$ (SEQ ID NO:52)

The desired product was prepared by substituting Fmoc-Arg(Pbf)-[4-(4-N-ethyl)methyl-3-methoxyphenoxy]butyryl AM resin ethylamide resin for Fmoc-Pro Sieber ethylamide resin, Fmoc-Gln(Trt) for Fmoc-Nva, and omitting the coupling with-Fmoc-Arg(Pmc) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Gln-Ile-Arg-NHCH$_2$CH$_3$ as the trifluoroacetate salt: $R_t$=2.771 minutes (gradient varying over 10 minutes from 20% to 80% acetonitrile/water containing 0.01% TFA); MS (ESI) m/e 586.3.

EXAMPLE 154

N-Ac-Thr-Nva-Ile-Arg-NHCH$_2$CH$_3$ (SEQ ID NO:53)

The desired product was prepared by substituting Fmoc-Arg(Pbf)-[4-(4-N-ethyl)methyl-3-methoxyphenoxy]butyryl AM resin ethylamide resin for Fmoc-Pro Sieber ethylamide resin and omitting the coupling with Fmoc-Arg(Pmc) in Example 43. After workup the crude peptide was purified by HPLC using a C-18 column and a solvent system varying in gradient over 50 minutes from 5% to 100% acetonitrile/water containing 0.01% TFA. The pure fractions were lyophilized to provide N-Ac-Thr-Nva-Ile-Arg-NHCH$_2$CH$_3$ as the trifluoroacetate salt: R$_t$=3.586 minutes (gradient varying over 10 minutes from 20% to 80% acetonitrile/water containing 0.01% TFA); MS (ESI) m/e 557.3.

EXAMPLE 155

N-Ac-D-Ile-Thr-Gln-Ile-Arg-NHCH$_2$CH$_3$

The desired product can be prepared by substituting Fmoc-Arg(Pbf)-[4-(4-N-ethyl)methyl-3-methoxyphenoxy]butyryl AM resin ethylamide resin for Fmoc-Pro Sieber ethylamide resin, Fmoc-Gln(Trt) for Fmoc-Nva, and omitting the coupling with Fmoc-Arg(Pmc) in Example 1. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Ile-Thr-Gln-Ile-Arg-NHCH$_2$CH$_3$ as the trifluoroacetate salt

EXAMPLE 156

N-Ac-D-Ile-Thr-Nva-Lys(Ac)-Arg-NHCH$_2$CH$_3$

The desired product can be prepared by substituting Fmoc-Arg(Pbf)-[4-(4-N-ethyl)methyl-3-methoxyphenoxy]butyryl AM resin ethylamide resin for Fmoc-Pro Sieber ethylamide resin, Fmoc-Lys(Ac) for Fmoc-Ile, and omitting the coupling with Fmoc-Arg(Pmc) in Example 1. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-IleThr-Nva-Lys(Ac)-Arg-NHCH$_2$CH$_3$ as the trifluoroacetate salt.

EXAMPLE 157

N-Ac-D-Ile-Ser-Gln-Ile-Arg-NHCH$_2$CH$_3$

The desired product can be prepared by substituting Fmoc-Arg(Pbf)-[4-(4-N-ethyl)methyl-3-methoxyphenoxy]butyryl AM resin ethylamide resin for Fmoc-Pro Sieber ethylamide resin, Fmoc-Ser(O-tBu) for Fmoc-Thr(O-tBu), Fmoc-Gln(Trt) for Fmoc-Nva, and omitting the coupling with Fmoc-Arg(Pmc) in Example 1. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Ile-Ser-Gln-Ile-Arg-NHCH$_2$CH$_3$ as the trifluoroacetate salt.

EXAMPLE 158

N-Ac-D-aIle-Ser-Ser-Ile-Arg-NHCH$_2$CH$_3$

The desired product can be prepared by substituting Fmoc-Arg(Pbf)-[4-(4-N-ethyl)methyl-3-methoxyphenoxy]butyryl AM resin ethylamide resin for Fmoc-Pro Sieber ethylamide resin, Fmoc-D-aIle for Fmoc-D-Ile, Fmoc-Ser(O-tBu) for Fmoc-Thr(O-tBu) and Fmoc-Nva, and omitting the coupling with Fmoc-Arg(Pmc) in Example 1. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-aIle-Ser-Ser-Ile-Arg-NHCH$_2$CH$_3$ as the trifluoroacetate salt.

EXAMPLE 159

N-Ac-D-aIle-Thr-Nva-Ile-Arg-NHCH$_2$CH$_3$

The desired product can be prepared by substituting Fmoc-Arg(Pbf)-[4-(4-N-ethyl)methyl-3-methoxyphenoxy]butyryl AM resin ethylamide resin for Fmoc-Pro Sieber ethylamide resin, Fmoc-D-aIle for Fmoc-D-Ile, and omitting the coupling with Fmoc-Arg(Pmc) in Example 1. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-aIle-Thr-Nva-Ile-Arg-NHCH$_2$CH$_3$ as the trifluoroacetate salt.

EXAMPLE 160

N-Ac-D-Ile-Thr-Gln-Lys(Ac)-Arg-NHCH$_2$CH$_3$

The desired product can be prepared by substituting Fmoc-Arg(Pbf)-[4-(4-N-ethyl)methyl-3-methoxyphenoxy]butyryl AM resin ethylamide resin for Fmoc-Pro Sieber ethylamide resin, Fmoc-Gln(Trt) for Fmoc-Nva, Fmoc-Lys(Ac) for Fmoc-Ile, and omitting the coupling with Fmoc-Arg(Pmc) in Example 1. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Ile-Thr-Gln-Lys(Ac)-Arg-NHCH$_2$CH$_3$ as the trifluoroacetate salt.

EXAMPLE 161

N-Ac-D-aIle-Ser-Nva-Lys(Ac)-Arg-NHCH$_2$CH$_3$

The desired product can be prepared by substituting Fmoc-Arg(Pbf)-[4-(4-N-ethyl)methyl-3-methoxyphenoxy]butyryl AM resin ethylamide resin for Fmoc-Pro Sieber ethylamide resin, Fmoc-D-aIle for Fmoc-D-Ile, Fmoc-Ser(O-tBu) for Fmoc-Thr(O-tBu), Fmoc-Lys(Ac) for Fmoc-Ile, and omitting the coupling with Fmoc-Arg(Pmc) in Example 1. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-aIle-Ser-Nva-Lys(Ac)-Arg-NHCH$_2$CH$_3$ as the trifluoroacetate salt.

EXAMPLE 162

N-Ac-D-Ile-Thr-Ser-Ile-Arg-NHCH$_2$CH$_3$

The desired product can be prepared by substituting Fmoc-Arg(Pbf)-[4-(4-N-ethyl)methyl-3-methoxyphenoxy]butyryl AM resin ethylamide resin for Fmoc-Pro Sieber ethylamide resin, Fmoc-Ser(O-tBu) for Fmoc-Nva, and omitting the coupling with Fmoc-Arg(Pmc) in Example 1.

After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Ile-Thr-Ser-Ile-Arg-NHCH$_2$CH$_3$ as the trifluoroacetate salt.

EXAMPLE 163

N-Ac-D-Ile-Thr-NMeNva-Ile-Arg-NHCH$_2$CH$_3$

The desired product can be prepared by substituting Fmoc-Arg(Pbf)-[4-(4-N-ethyl)methyl-3-methoxyphenoxy]butyryl AM resin ethylamide resin for Fmoc-Pro Sieber ethylamide resin, Fmoc-NMeNva for Fmoc-Nva, omitting the coupling with Fmoc-Arg(Pmc), and using HATU instead of HBTU in the coupling of the N-methyl-amino acid in Example 1. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Ile-Thr-NMeNva-Ile-Arg-NHCH$_2$CH$_3$ as the trifluoroacetate salt.

EXAMPLE 164

N-Ac-Ser-Gln-Ile-Arg-NHCH$_2$CH$_3$ (SEQ ID NO:54)

The desired product can be prepared by substituting Fmoc-Arg(Pbf)-[4-(4-N-ethyl)methyl-3-methoxyphenoxy]butyryl AM resin ethylamide resin for Fmoc-Pro Sieber ethylamide resin, Fmoc-Ser(O-tBu) for Fmoc-Thr(O-tBu), Fmoc-Gln(Trt) for Fmoc-Nva, and omitting the coupling with Fmoc-Arg(Pmc) in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-Ser-Gln-Ile-Arg-NHCH$_2$CH$_3$ as the trifluoroacetate salt.

EXAMPLE 165

N-Ac-Ser-Ser-Ile-Arg-NHCH$_2$CH$_3$ (SEQ ID NO:55)

The desired product can be prepared by substituting Fmoc-Arg(Pbf)-[4-(4-N-ethyl)methyl-3-methoxyphenoxy]butyryl AM resin ethylamide resin for Fmoc-Pro Sieber ethylamide resin, Fmoc-Ser(O-tBu) for Fmoc-Thr(O-tBu) and Fmoc-Nva, and omitting the coupling with Fmoc-Arg(Pmc) in Example 43 After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-Ser-Ser-Ile-Arg-NHCH$_2$CH$_3$ as the trifluoroacetate salt.

EXAMPLE 166

N-Ac-Thr-Nva-Lys(Ac)-Arg-NH$_2$CH$_3$ (SEQ ID NO:56)

The desired product can be prepared by substituting Fmoc-Arg(Pbf)-[4-(4-N-ethyl)methyl-3-methoxyphenoxy]butyryl AM resin ethylamide resin for Fmoc-Pro Sieber ethylamide resin, Fmoc-Lys(Ac) for Fmoc-Ile, and omitting the coupling with Fmoc-Arg(Pmc) in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-Thr-Nva-Lys(Ac)-Arg-NHCH$_2$CH$_3$ as the trifluoroacetate salt.

EXAMPLE 167

N-Ac-Thr-Gln-Lys(Ac)-Arg-NHCH$_2$CH$_3$ (SEQ ID NO:57)

The desired product can be prepared by substituting Fmoc-Arg(Pbf)-[4-(4-N-ethyl)methyl-3-methoxyphenoxy]butyryl AM resin ethylamide resin for Fmoc-Pro Sieber ethylamide resin, Fmoc-Gln(Trt) for Fmoc-Nva, Fmoc-Lys(Ac) for Fmoc-Ile, and omitting the coupling with Fmoc-Arg(Pmc) in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-Thr-Gln-Lys(Ac)-Arg-NHCH$_2$CH$_3$ as the trifluoroacetate salt

EXAMPLE 168

N-Ac-Thr-Ser-Ile-Arg-NHCH$_2$CH$_3$ (SEQ ID NO:58)

The desired product can be prepared by substituting Fmoc-Arg(Pbf)-[4-(4-N-ethyl)methyl-3-methoxyphenoxy]butyryl AM resin ethylamide resin for Fmoc-Pro Sieber ethylamide resin, Fmoc-Ser(O-tBu) for Fmoc-Nva, and omitting the coupling with Fmoc-Arg(Pmc) in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-Thr-Ser-Ile-Arg-NHCH$_2$CH$_3$ as the trifluoroacetate salt.

EXAMPLE 169

N-Ac-Met-Nva-Ile-Arg-NHCH$_2$CH$_3$ (SEQ ID NO:59)

The desired product can be prepared by substituting Fmoc-Arg(Pbf)-[4-(4-N-ethyl)methyl-3-methoxyphenoxy]butyryl AM resin ethylamide resin for Fmoc-Pro Sieber ethylamide resin, Fmoc-Met for Fmoc-Thr(O-tBu), and omitting the coupling with Fmoc-Arg(Pmc) in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-Met-Nva-Ile-Arg-NHCH$_2$CH$_3$ as the trifluoroacetate salt.

EXAMPLE 170

N-Ac-Thr-NMeNva-Ile-Arg-NHCH$_2$CH$_3$ (SEQ ID NO:60)

The desired product can be prepared by substituting Fmoc-Arg(Pbf)-[4-(4-N-ethyl)methyl-3-methoxyphenoxy]butyryl AM resin ethylamide resin for Fmoc-Pro Sieber ethylamide resin and Fmoc-NMeNva for Fmoc-Nva, omitting the coupling with Fmoc-Arg(Pmc), and using HATU instead of HBTU in the coupling of the N-methyl-amino acid in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Thr-NMeNva-Ile-Arg-NHCH$_2$CH$_3$ as the trifluoroacetate salt.

EXAMPLE 171

N-Ac-D-Nva-Gln-Ile-Arg-NHCH$_2$CH$_3$

The desired product can be prepared by substituting Fmoc-Arg(Pbf)-[4-(4-N-ethyl)methyl-3-methoxyphenoxy] butyryl AM resin ethylamide resin for Fmoc-Pro Sieber ethylamide resin, Fmoc-D-Nva for Fmoc-Thr(O-tBu), Fmoc-Gln(Trt) for Fmoc-Nva, and omitting the coupling with Fmoc-Arg(Pmc) in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide NAc-D-Nva-Gln-Ile-Arg-NHCH$_2$CH$_3$ as the trifluoroacetate salt.

EXAMPLE 172

N-Ac-Ser-Nva-Ile-Arg-NHCH$_2$CH$_3$ (SEQ ID NO:61)

The desired product can be prepared by substituting Fmoc-Arg(Pbf)-[4-(4-N-ethyl)methyl-3-methoxyphenoxy] butyryl AM resin ethylamide resin for Fmoc-Pro Sieber ethylamide resin, Fmoc-Ser(O-tBu) for Fmoc-Thr(O-tBu), and omitting the coupling with Fmoc-Arg(Pmc) in Example 43. After workup the crude peptide can be purified by HPLC using a C-18 column and a solvent system varying in gradient over 50 minutes from 5% to 100% acetonitrile/ water containing 0.01% TFA. The pure fractions can be lyophilized to provide N-Ac-Ser-Nva-Ile-Arg-NHCH$_2$CH$_3$ as the trifluoroacetate salt.

EXAMPLE 173

N-Ac-D-Thr-Gln-Ile-Arg-NHCH$_2$CH$_3$

The desired product can be prepared by substituting Fmoc-Arg(Pbf)-[4-(4-N-ethyl)methyl-3-methoxyphenoxy] butyryl AM resin ethylamide resin for Fmoc-Pro Sieber ethylamide resin, Fmoc-D-Thr(O-tBu) for Fmoc-Thr(O-tBu), Fmoc-Gln(Trt) for Fmoc-Nva, and omitting the coupling with Fmoc-Arg(Pmc) in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Thr-Gln-Ile-Arg-NHCH$_2$CH$_3$ as the trifluoroacetate salt.

EXAMPLE 174

N-Ac-D-Ser-Gln-Ile-Arg-NHCH$_2$CH$_3$

The desired product can be prepared by substituting Fmoc-Arg(Pbf)-[4-(4-N-ethyl)methyl-3-methoxyphenoxy] butyryl AM resin ethylamide resin for Fmoc-Pro Sieber ethylamide resin, Fmoc-DSer(O-tBu) for Fmoc-Thr(O-tBu), Fmoc-Gln(Trt) for Fmoc-Nva, and omitting the coupling with Fmoc-Arg(Pmc) in Example 43. After workup the crude peptide can be purified by HPLC using a C-18 column and a solvent system varying in gradient over 50 minutes from 5% to 100% acetonitrile/water containing 0.01% TFA. The pure fractions can be lyophilized to provide N-Ac-D-Ser-Gln-Ile-Arg-NHCH$_2$ CH$_3$ as the trifluoroacetate salt.

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

---

SEQUENCE LISTING

```
<160> NUMBER OF SEQ ID NOS: 61

<210> SEQ ID NO 1
<211> LENGTH: 8
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = R-(CH2)n-C(O)-, wherein n is an integer
      from 0 to 8, R is alkoxy, alkyl, amino, aryl, carboxyl,
      cycloalkenyl, cycloalkyl, and heterocycle at
      position 1
<220> FEATURE:
<221> NAME/KEY: VARIANT
<222> LOCATION: (2)...(2)
<223> OTHER INFORMATION: Xaa = bAla and Ile at position 2
<220> FEATURE:
<221> NAME/KEY: VARIANT
<222> LOCATION: (3)...(3)
<223> OTHER INFORMATION: Xaa = alloThr, AllylGly, Asn, Asp, Gln,
```

```
          N-methylglutaminyl, Glu, N-methylglutamyl, Gly,
          His, Hser, Ile, Lys(Ac), Met, Nle, Nva, Sar, Ser,
          N-methylseryl, Thr, Trp and Tyr at position 3
<220> FEATURE:
<221> NAME/KEY: VARIANT
<222> LOCATION: (3)...(3)
<223> OTHER INFORMATION: 3 (Continued)
          Xaa = tyrosyl(O-methyl) at position 3
<220> FEATURE:
<221> NAME/KEY: VARIANT
<222> LOCATION: (4)...(4)
<223> OTHER INFORMATION: Xaa = N-methylalanyl, alloThr, Arg, Asn, Cit,
          Gln, Glu, Gly, Hser, Leu, Lys(Ac), Lys(Nic), Nle, Nva,
          NMeNva, Orn(Ac), 3-Pal, Sar, Ser, N-methylseryl, Thr, Trp, Val
          and N-methylvalyl at position 4
<220> FEATURE:
<221> NAME/KEY: VARIANT
<222> LOCATION: (5)...(5)
<223> OTHER INFORMATION: Xaa = Ala, aIle, Asp, Cit, Gln, Ile,
          N-methylisoleucyl, Leu, Lys, Lys(Ac), Nle, Nva,
          Phe, Pro and Val at position 5
<220> FEATURE:
<221> NAME/KEY: VARIANT
<222> LOCATION: (6)...(6)
<223> OTHER INFORMATION: Xaa = Arg, Cit, His, Lys, Lys(Isp), Orn and
          3-Pal at position 6
<220> FEATURE:
<221> NAME/KEY: VARIANT
<222> LOCATION: (7)...(7)
<223> OTHER INFORMATION: Xaa = 2-aminobutyryl, 2-aminoisobutyryl,
          homoprolyl, hydroxyprolyl, Leu, Phe, Pro and Thr
          at position 7
<220> FEATURE:
<221> NAME/KEY: VARIANT
<222> LOCATION: (8)...(8)
<223> OTHER INFORMATION: Xaa = azaglycylamide, glycylamide, hydroxyl,
          -NH-(CH2)n-CHR1R2, -NHR3, wherein n is an integer
          from 0 to 8, R1 is hydrogen, alkyl, cycloalkenyl,
          and cycloalkyl at position 8
<220> FEATURE:
<221> NAME/KEY: VARIANT
<222> LOCATION: (8)...(8)
<223> OTHER INFORMATION: 8 (Continued)
          Xaa = R2 is hydrogen, alkoxy, alkyl, aryl,
          cycloalkenyl, cycloalkyl, heterocycle, and
          hydroxyl, provided that when n is 0, R2 is other
          than alkoxy or hydroxyl at position 8
<220> FEATURE:
<221> NAME/KEY: VARIANT
<222> LOCATION: (8)...(8)
<223> OTHER INFORMATION: 8 (Continued)
          Xaa = R3 is hydrogen, cycloalkenyl, cycloalkyl and
          hydroxyl, and provided that when Xaa6 is
          D-alloisoleucyl, Xaa7 is threonyl and Xaa8 is
          hydroxyl at position 8

<400> SEQUENCE: 1

Xaa Xaa Xaa Xaa Xaa Xaa Xaa Xaa
 1               5

<210> SEQ ID NO 2
<211> LENGTH: 8
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = R-(CH2)n-C(O)-, wherein n is an integer
          from 0 to 8, R is alkoxy, alkyl, amino, aryl, carboxyl,
          cycloalkenyl, cycloalkyl, and heterocycle at position 1
<220> FEATURE:
<221> NAME/KEY: VARIANT
<222> LOCATION: (2)...(2)
<223> OTHER INFORMATION: Xaa = bAla and Ile at position 2
<220> FEATURE:
```

```
<221> NAME/KEY: VARIANT
<222> LOCATION: (3)...(3)
<223> OTHER INFORMATION: Xaa = alloThr,  Asp, Gln, N-methylglutaminyl,
      Gly, His, Hser, Ile, Lys(Ac), Met, Ser, N-methylseryl, Thr, Trp,
      Tyr, and tyrosyl(O-methyl) at position 3
<220> FEATURE:
<221> NAME/KEY: VARIANT
<222> LOCATION: (4)...(4)
<223> OTHER INFORMATION: Xaa = N-methylalanyl, alloThr, Arg, Gln, Gly,
      Hser, Leu, Lys(Ac), Nle, Nva, NMeNva, Orn(Ac),
      3-Pal, Sar, Ser, N-methylseryl, Thr, Trp, Val and
      N-methylvalyl at position 4
<220> FEATURE:
<221> NAME/KEY: VARIANT
<222> LOCATION: (5)...(5)
<223> OTHER INFORMATION: Xaa = Ala, aIle, Asp, Cit, Gln,  Ile,
      N-methylisoleucyl, Leu, Lys, Lys(Ac), Nle, Nva,
      Phe, and Pro at position 5
<220> FEATURE:
<221> NAME/KEY: VARIANT
<222> LOCATION: (6)...(6)
<223> OTHER INFORMATION: Xaa = Arg, Cit, His, Lys, Lys(Isp), Orn,
      and 3-Pal at position 6
<220> FEATURE:
<221> NAME/KEY: VARIANT
<222> LOCATION: (7)...(7)
<223> OTHER INFORMATION: Xaa = 2-aminobutyryl, 2-aminoisobutyryl,
      homoprolyl, hydroxyprolyl, Leu, Phe, and Pro at
      position 7
<220> FEATURE:
<221> NAME/KEY: VARIANT
<222> LOCATION: (8)...(8)
<223> OTHER INFORMATION: Xaa = azaglycylamide, glycylamide, hydroxyl,
      -NH-(CH2)n-CHR1R2, -NHR3, wherein n is an integer
      from 0 to 8, R1 is hydrogen, alkyl, cycloalkenyl,
      and cycloalkyl at position 8
<220> FEATURE:
<221> NAME/KEY: VARIANT
<222> LOCATION: (8)...(8)
<223> OTHER INFORMATION: 8 (Continued)
      Xaa = R2 is hydrogen, alkoxy, or alkyl, aryl,
      cycloalkenyl, cycloalkyl, heterocycle, and
      hydroxyl at position 8
<220> FEATURE:
<221> NAME/KEY: VARIANT
<222> LOCATION: (8)...(8)
<223> OTHER INFORMATION: 8 (Continued)
      Xaa = with the proviso that when n is 0, R2 is
      other than alkoxy and hydroxyl at position 8
<220> FEATURE:
<221> NAME/KEY: VARIANT
<222> LOCATION: (8)...(8)
<223> OTHER INFORMATION: 8 (Continued)
      Xaa = R3 is hydrogen, cycloalkenyl, cycloalkyl,
      and hydroxyl at position 8

<400> SEQUENCE: 2

Xaa Xaa Xaa Xaa Xaa Xaa Xaa Xaa
 1               5

<210> SEQ ID NO 3
<211> LENGTH: 7
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = R-(CH2)n-C(O)-, wherein n is an integer
      from 0 to 8, R is alkoxy, alkyl, amino, aryl, carboxyl,
      cycloalkenyl, cycloalkyl, and heterocycle at position 1
<220> FEATURE:
<221> NAME/KEY: VARIANT
<222> LOCATION: (2)...(2)
<223> OTHER INFORMATION: Xaa = alloThr, AllylGly, Asn, Asp, Gln, Glu,
      N-methylglutamyl, Gly, His, Hser, Ile, Lys(Ac),
```

```
        Met, Nle, Nva, Sar, Ser, N-methylseryl, Thr, Trp,
        Tyr and tyrosyl(O-methyl) at position 2
<220> FEATURE:
<221> NAME/KEY: VARIANT
<222> LOCATION: (3)...(3)
<223> OTHER INFORMATION: Xaa = N-methylalanyl, alloThr, Arg, Asn, Cit,
        Gln, Glu, Gly, Hser, Leu, Lys(Ac), Lys(Nic), Nle, Nva, NMeNva,
        Orn(Ac), 3-Pal, Sar, and Ser at position 3
<220> FEATURE:
<221> NAME/KEY: VARIANT
<222> LOCATION: (3)...(3)
<223> OTHER INFORMATION: 3  (Continued)
        Xaa = N-methylseryl, Thr, Trp, Val and
        N-methylvalyl at position 3
<220> FEATURE:
<221> NAME/KEY: VARIANT
<222> LOCATION: (4)...(4)
<223> OTHER INFORMATION: Xaa = Ala, aIle, Asp, Cit, Ile,
        N-methylisoleucyl, Leu, Lys, Lys(Ac), Nva, Phe, Pro and Val at
        position 4
<220> FEATURE:
<221> NAME/KEY: VARIANT
<222> LOCATION: (5)...(5)
<223> OTHER INFORMATION: Xaa = Arg, Cit, His, Lys, Lys(Isp), Orn and
        3-Pal at position 5
<220> FEATURE:
<221> NAME/KEY: VARIANT
<222> LOCATION: (6)...(6)
<223> OTHER INFORMATION: Xaa = 2-aminobutyryl, 2-aminoisobutyryl,
        homoprolyl, hydroxyprolyl, Leu, Phe, Pro and Thr
        at position 6
<220> FEATURE:
<221> NAME/KEY: VARIANT
<222> LOCATION: (7)...(7)
<223> OTHER INFORMATION: Xaa = azaglycylamide, glycylamide, hydroxyl,
        -NH-(CH2)n-CHR1R2, -NHR3, wherein n is an integer
        from 0 to 8, R1 is hydrogen, alkyl, cycloalkenyl,
        and cycloalkyl at position 7
<220> FEATURE:
<221> NAME/KEY: VARIANT
<222> LOCATION: (7)...(7)
<223> OTHER INFORMATION: 7  (Continued)
        Xaa = R2 is hydrogen, alkoxy, or alkyl, aryl,
        cycloalkenyl, cycloalkyl, heterocycle, and
        hydroxyl at position 7
<220> FEATURE:
<221> NAME/KEY: VARIANT
<222> LOCATION: (7)...(7)
<223> OTHER INFORMATION: 7  (Continued)
        Xaa = with the proviso that when n is 0, R2 is
        other than alkoxy and hydroxyl at position 7
<220> FEATURE:
<221> NAME/KEY: VARIANT
<222> LOCATION: (7)...(7)
<223> OTHER INFORMATION: 7  (Continued)
        Xaa = R3 is hydrogen, cycloalkenyl, cycloalkyl and
        hydroxyl, provided that when Xaa5 is
        D-alloisoleucyl, Xaa6 is threonyl and Xaa7 is
        hydroxyl at position 7

<400> SEQUENCE: 3

Xaa Xaa Xaa Xaa Xaa Xaa Xaa
 1               5

<210> SEQ ID NO 4
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
```

<223> OTHER INFORMATION: Xaa = prolytheylamide at position 5

<400> SEQUENCE: 4

Thr Xaa Ile Arg Xaa
 1               5

<210> SEQ ID NO 5
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = alloThr at position 1
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = prolyltheylamide at position 5

<400> SEQUENCE: 5

Xaa Xaa Ile Arg Xaa
 1               5

<210> SEQ ID NO 6
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (5)...(5)
<223> OTHER INFORMATION: Xaa = prolylethylamide at position 5

<400> SEQUENCE: 6

Thr Gln Ile Arg Xaa
 1               5

<210> SEQ ID NO 7
<211> LENGTH: 6
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = N-(6-methylnicotinyl) at position 1
<220> FEATURE:
<221> NAME/KEY: VARIANT
<222> LOCATION: (3)...(3)
<223> OTHER INFORMATION: Xaa = Nva at position 3
<220> FEATURE:
<221> NAME/KEY: VARIANT
<222> LOCATION: (6)...(6)
<223> OTHER INFORMATION: Xaa = prolylethylamide at position 6

<400> SEQUENCE: 7

Xaa Thr Xaa Ile Arg Xaa
 1               5

<210> SEQ ID NO 8
<211> LENGTH: 5
<212> TYPE: PRT
<213> ORGANISM: Artificial Sequence

```
<220> FEATURE:
<223> OTHER INFORMATION: Antiangiogenic Peptide
<220> FEATURE:
<221> NAME/KEY: VARIANT
<222> LOCATION: (5)...(5)
<223> OTHER INFORMATION: Xaa = prolylethylamide at position 5

<400> SEQUENCE: 8

Ser Ser Ile Arg Xaa
 1               5

<210> SEQ ID NO 9
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (5)...(5)
<223> OTHER INFORMATION: Xaa = prolylethylamide at position 5

<400> SEQUENCE: 9

Thr Ser Ile Arg Xaa
 1               5

<210> SEQ ID NO 10
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = NMeNva at position 2
<220> FEATURE:
<221> NAME/KEY: VARIANT
<222> LOCATION: (5)...(5)
<223> OTHER INFORMATION: Xaa = prolylethylamide at position 5

<400> SEQUENCE: 10

Thr Xaa Ile Arg Xaa
 1               5

<210> SEQ ID NO 11
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: CONFLICT
<222> LOCATION: (5)...(5)
<223> OTHER INFORMATION: Xaa = prolylethylamide at position 5

<400> SEQUENCE: 11

Tyr Xaa Ile Arg Xaa
 1               5

<210> SEQ ID NO 12
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
```

```
<221> NAME/KEY: VARIANT
<222> LOCATION: (5)...(5)
<223> OTHER INFORMATION: Xaa = prolylethylamide at position 5

<400> SEQUENCE: 12

Ser Gln Ile Arg Xaa
 1               5

<210> SEQ ID NO 13
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (3)...(3)
<223> OTHER INFORMATION: Xaa = Lys(Ac) at position 3
<220> FEATURE:
<221> NAME/KEY: VARIANT
<222> LOCATION: (5)...(5)
<223> OTHER INFORMATION: Xaa = prolylethylamide at position 5

<400> SEQUENCE: 13

Thr Xaa Xaa Arg Xaa
 1               5

<210> SEQ ID NO 14
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (5)...(5)
<223> OTHER INFORMATION: Xaa = prolylethylamide at position 5

<400> SEQUENCE: 14

Ser Thr Ile Arg Xaa
 1               5

<210> SEQ ID NO 15
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = NMeGlu at position 1
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = prolylethylamide at position 5

<400> SEQUENCE: 15

Xaa Xaa Ile Arg Xaa
 1               5

<210> SEQ ID NO 16
<211> LENGTH: 5
```

<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = prolylethylamide at position 5

<400> SEQUENCE: 16

Met Xaa Ile Arg Xaa
 1 5

<210> SEQ ID NO 17
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = Lys(Ac) at position 1
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = prolylethylamide at position 5

<400> SEQUENCE: 17

Xaa Xaa Ile Arg Xaa
 1 5

<210> SEQ ID NO 18
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = prolylethylamide at position 5

<400> SEQUENCE: 18

Gln Xaa Ile Arg Xaa
 1 5

<210> SEQ ID NO 19
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = alloThr at position 1
<220> FEATURE:
<221> NAME/KEY: VARIANT
<222> LOCATION: (5)...(5)
<223> OTHER INFORMATION: Xaa = prolylethylamide at position 5

```
<400> SEQUENCE: 19

Xaa Ser Ile Arg Xaa
 1               5

<210> SEQ ID NO 20
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = alloThr at position 1
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = prolylethylamide at position 5

<400> SEQUENCE: 20

Xaa Xaa Pro Arg Xaa
 1               5

<210> SEQ ID NO 21
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = prolylethylamide at position 5

<400> SEQUENCE: 21

Trp Xaa Ile Arg Xaa
 1               5

<210> SEQ ID NO 22
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nle at position 2
<220> FEATURE:
<221> NAME/KEY: VARIANT
<222> LOCATION: (5)...(5)
<223> OTHER INFORMATION: Xaa = prolylethylamide at position 5

<400> SEQUENCE: 22

Thr Xaa Ile Arg Xaa
 1               5

<210> SEQ ID NO 23
<211> LENGTH: 5
<212> TYPE: PRT
<213> ORGANISM: Artificial Sequence
<220> FEATURE:
```

```
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = prolylethylamide at position 5

<400> SEQUENCE: 23

Thr Xaa Pro Arg Xaa
 1               5

<210> SEQ ID NO 24
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (3)...(3)
<223> OTHER INFORMATION: Xaa = Lys(Ac) at position 3
<220> FEATURE:
<221> NAME/KEY: VARIANT
<222> LOCATION: (5)...(5)
<223> OTHER INFORMATION: Xaa = prolylethylamide at position 5

<400> SEQUENCE: 24

Ser Gln Xaa Arg Xaa
 1               5

<210> SEQ ID NO 25
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = allylGly at position 1
<220> FEATURE:
<221> NAME/KEY: VARIANT
<222> LOCATION: (5)...(5)
<223> OTHER INFORMATION: Xaa = prolylethylamide at position 5

<400> SEQUENCE: 25

Xaa Gln Ile Arg Xaa
 1               5

<210> SEQ ID NO 26
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = prolylethylamide at position 5

<400> SEQUENCE: 26

Thr Xaa Lys Arg Xaa
 1               5
```

```
<210> SEQ ID NO 27
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (4)...(4)
<223> OTHER INFORMATION: Xaa = Orn at position 4
<220> FEATURE:
<221> NAME/KEY: VARIANT
<222> LOCATION: (5)...(5)
<223> OTHER INFORMATION: Xaa = proethylamide at position 5

<400> SEQUENCE: 27

Thr Xaa Ile Xaa Xaa
 1               5

<210> SEQ ID NO 28
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = proethylamide at position 5

<400> SEQUENCE: 28

Glu Xaa Ile Arg Xaa
 1               5

<210> SEQ ID NO 29
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = proethylamide at position 5

<400> SEQUENCE: 29

Asn Xaa Ile Arg Xaa
 1               5

<210> SEQ ID NO 30
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = Hser at position 1
<220> FEATURE:
<221> NAME/KEY: VARIANT
```

```
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = proethylamide at position 5

<400> SEQUENCE: 30

Xaa Xaa Ile Arg Xaa
 1               5

<210> SEQ ID NO 31
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = Sar at position 1
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = proethylamide at position 5

<400> SEQUENCE: 31

Xaa Xaa Ile Arg Xaa
 1               5

<210> SEQ ID NO 32
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = proethylamide at position 5

<400> SEQUENCE: 32

Asp Xaa Ile Arg Xaa
 1               5

<210> SEQ ID NO 33
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (3)...(3)
<223> OTHER INFORMATION: Xaa = Nva at position 3
<220> FEATURE:
<221> NAME/KEY: VARIANT
<222> LOCATION: (5)...(5)
<223> OTHER INFORMATION: Xaa = proethylamide at position 5

<400> SEQUENCE: 33

Ser Gln Xaa Arg Xaa
 1               5
```

```
<210> SEQ ID NO 34
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (4)...(4)
<223> OTHER INFORMATION: Xaa = Cit
<220> FEATURE:
<221> NAME/KEY: VARIANT
<222> LOCATION: (5)...(5)
<223> OTHER INFORMATION: Xaa = proethylamide at position 5

<400> SEQUENCE: 34

Ser Gln Ile Xaa Xaa
 1               5

<210> SEQ ID NO 35
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (4)...(4)
<223> OTHER INFORMATION: Xaa = 3Pal at position 4
<220> FEATURE:
<221> NAME/KEY: VARIANT
<222> LOCATION: (5)...(5)
<223> OTHER INFORMATION: Xaa = proethylamide at position 5

<400> SEQUENCE: 35

Ser Gln Ile Xaa Xaa
 1               5

<210> SEQ ID NO 36
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (3)...(3)
<223> OTHER INFORMATION: Xaa = Nva at position 3
<220> FEATURE:
<221> NAME/KEY: VARIANT
<222> LOCATION: (5)...(5)
<223> OTHER INFORMATION: Xaa = proethylamide at position 5

<400> SEQUENCE: 36

Thr Gln Xaa Arg Xaa
 1               5

<210> SEQ ID NO 37
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (5)...(5)
<223> OTHER INFORMATION: Xaa = proethylamide at position 5

<400> SEQUENCE: 37

Thr Asn Ile Arg Xaa
 1               5
```

<210> SEQ ID NO 38
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = proethylamide at position 5

<400> SEQUENCE: 38

Thr Xaa Pro Arg Xaa
 1               5

<210> SEQ ID NO 39
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = Nva at position 1
<220> FEATURE:
<221> NAME/KEY: VARIANT
<222> LOCATION: (5)...(5)
<223> OTHER INFORMATION: Xaa = proethylamide at position 5

<400> SEQUENCE: 39

Xaa Gln Ile Arg Xaa
 1               5

<210> SEQ ID NO 40
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (4)...(4)
<223> OTHER INFORMATION: Xaa = Cit at position 4
<220> FEATURE:
<221> NAME/KEY: VARIANT
<222> LOCATION: (5)...(5)
<223> OTHER INFORMATION: Xaa = proethylamide at position 5

<400> SEQUENCE: 40

Thr Arg Ile Xaa Xaa
 1               5

<210> SEQ ID NO 41
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (3)...(3)
<223> OTHER INFORMATION: Xaa = Lys(Ac) at position 3
<220> FEATURE:
<221> NAME/KEY: VARIANT
<222> LOCATION: (5)...(5)
<223> OTHER INFORMATION: Xaa = proethylamide at position 5

```
<400> SEQUENCE: 41

Thr Gln Xaa Arg Xaa
1               5

<210> SEQ ID NO 42
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (3)...(3)
<223> OTHER INFORMATION: Xaa = Lys(Ac) at position 3
<220> FEATURE:
<221> NAME/KEY: VARIANT
<222> LOCATION: (5)...(5)
<223> OTHER INFORMATION: Xaa = proethylamide at position 5

<400> SEQUENCE: 42

Thr Ser Xaa Arg Xaa
1               5

<210> SEQ ID NO 43
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Cit at position 2
<220> FEATURE:
<221> NAME/KEY: VARIANT
<222> LOCATION: (5)...(5)
<223> OTHER INFORMATION: Xaa = proethylamide at position 5

<400> SEQUENCE: 43

Thr Xaa Ile Arg Xaa
1               5

<210> SEQ ID NO 44
<211> LENGTH: 6
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = N-3Mev at position 1
<220> FEATURE:
<221> NAME/KEY: VARIANT
<222> LOCATION: (6)...(6)
<223> OTHER INFORMATION: Xaa = proethylamide at position 6

<400> SEQUENCE: 44

Xaa Thr Gln Ile Arg Xaa
1               5

<210> SEQ ID NO 45
<211> LENGTH: 6
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
```

```
<223> OTHER INFORMATION: Xaa = N-3Mev at position 1
<220> FEATURE:
<221> NAME/KEY: VARIANT
<222> LOCATION: (3)...(3)
<223> OTHER INFORMATION: Xaa = Nva at position 3
<220> FEATURE:
<221> NAME/KEY: VARIANT
<222> LOCATION: (6)...(6)
<223> OTHER INFORMATION: Xaa = proethylamide at position 6

<400> SEQUENCE: 45

Xaa Thr Xaa Ile Arg Xaa
 1               5

<210> SEQ ID NO 46
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (5)...(5)
<223> OTHER INFORMATION: Xaa = proethylamide at position 5

<400> SEQUENCE: 46

Ser Trp Ile Arg Xaa
 1               5

<210> SEQ ID NO 47
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (5)...(5)
<223> OTHER INFORMATION: Xaa = proethylamide at position 5

<400> SEQUENCE: 47

Thr Trp Ile Arg Xaa
 1               5

<210> SEQ ID NO 48
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Lys(Ac) at position 2
<220> FEATURE:
<221> NAME/KEY: VARIANT
<222> LOCATION: (5)...(5)
<223> OTHER INFORMATION: Xaa = proethylamide at position 5

<400> SEQUENCE: 48

Thr Xaa Ile Arg Xaa
 1               5

<210> SEQ ID NO 49
<211> LENGTH: 6
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
```

```
<222> LOCATION: (1)...(1)
<223> OTHER INFORMATION: Xaa = bAla at position 1
<220> FEATURE:
<221> NAME/KEY: VARIANT
<222> LOCATION: (3)...(3)
<223> OTHER INFORMATION: Xaa = Nva at position 3
<220> FEATURE:
<221> NAME/KEY: VARIANT
<222> LOCATION: (6)...(6)
<223> OTHER INFORMATION: Xaa = proethylamide at position 6

<400> SEQUENCE: 49

Xaa Thr Xaa Ile Arg Xaa
 1           5

<210> SEQ ID NO 50
<211> LENGTH: 6
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = bAla at position 1
<220> FEATURE:
<221> NAME/KEY: VARIANT
<222> LOCATION: (6)...(6)
<223> OTHER INFORMATION: Xaa = proethylamide at position 6

<400> SEQUENCE: 50

Xaa Thr Gln Ile Arg Xaa
 1           5

<210> SEQ ID NO 51
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (1)...(1)
<223> OTHER INFORMATION: Xaa = Nle at position 1
<220> FEATURE:
<221> NAME/KEY: VARIANT
<222> LOCATION: (5)...(5)
<223> OTHER INFORMATION: Xaa = proethylamide at position 5

<400> SEQUENCE: 51

Xaa Gln Ile Arg Xaa
 1               5

<210> SEQ ID NO 52
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (5)...(5)
<223> OTHER INFORMATION: Xaa = NHCH2CH3 at position 5

<400> SEQUENCE: 52

Thr Gln Ile Arg Xaa
 1               5

<210> SEQ ID NO 53
<211> LENGTH: 5
<212> TYPE: PRT
```

```
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = NHCH2CH3 at position 5

<400> SEQUENCE: 53

Thr Xaa Ile Arg Xaa
 1               5

<210> SEQ ID NO 54
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (5)...(5)
<223> OTHER INFORMATION: Xaa = NHCH2CH3 at position 5

<400> SEQUENCE: 54

Ser Gln Ile Arg Xaa
 1               5

<210> SEQ ID NO 55
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (5)...(5)
<223> OTHER INFORMATION: Xaa = NHCH2CH3 at position 5

<400> SEQUENCE: 55

Ser Ser Ile Arg Xaa
 1               5

<210> SEQ ID NO 56
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (3)...(3)
<223> OTHER INFORMATION: Xaa = Lys(Ac) at position 3
<220> FEATURE:
<221> NAME/KEY: VARIANT
<222> LOCATION: (5)...(5)
<223> OTHER INFORMATION: Xaa = NHCH2CH3 at position 5

<400> SEQUENCE: 56

Thr Xaa Xaa Arg Xaa
 1               5

<210> SEQ ID NO 57
<211> LENGTH: 5
```

```
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (3)...(3)
<223> OTHER INFORMATION: Xaa = Lys(Ac) at position 3
<220> FEATURE:
<221> NAME/KEY: VARIANT
<222> LOCATION: (5)...(5)
<223> OTHER INFORMATION: Xaa = NHCH2CH3 at position 5

<400> SEQUENCE: 57

Thr Gln Xaa Arg Xaa
 1               5

<210> SEQ ID NO 58
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (5)...(5)
<223> OTHER INFORMATION: Xaa = NHCH2CH3 at position 5

<400> SEQUENCE: 58

Thr Ser Ile Arg Xaa
 1               5

<210> SEQ ID NO 59
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = NHCH2CH3 at position 5

<400> SEQUENCE: 59

Met Xaa Ile Arg Xaa
 1               5

<210> SEQ ID NO 60
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = NMeNva at position 2
<220> FEATURE:
<221> NAME/KEY: VARIANT
<222> LOCATION: (5)...(5)
<223> OTHER INFORMATION: Xaa = NHCH2CH3 at position 5

<400> SEQUENCE: 60

Thr Xaa Ile Arg Xaa
 1               5

<210> SEQ ID NO 61
```

```
<211> LENGTH: 5
<212> TYPE: PRT
<213> ORGANISM: Artificial Sequence
<220> FEATURE:
<223> OTHER INFORMATION: Antiangiogenic Peptide
<220> FEATURE:
<221> NAME/KEY: VARIANT
<222> LOCATION: (2)...(2)
<223> OTHER INFORMATION: Xaa = Nva at position 2
<220> FEATURE:
<221> NAME/KEY: VARIANT
<222> LOCATION: (5)...(5)
<223> OTHER INFORMATION: Xaa = NHCH2CH3 at position 5

<400> SEQUENCE: 61

Ser Xaa Ile Arg Xaa
1               5
```

What is claimed is:

1. A compound of formula (II)

$$Xaa_1\text{-}Xaa_2\text{-}Xaa_3\text{-}Xaa_4\text{-}Xaa_5\text{-}Xaa_6\text{-}Xaa_7\text{-}Xaa_8 \quad \text{(II), (SEQ ID NO:2)}$$

or a therapeutically acceptable salt thereof, wherein $Xaa_1$ is selected from the group consisting of hydrogen and $R\text{—}(CH_2)_n\text{—}C(O)\text{—}$, wherein n is an integer from 0 to 8 and R is selected from the group consisting of alkoxy, alkyl, amino, aryl, carboxyl, cycloalkenyl, cycloalkyl, and heterocycle;

$Xaa_2$ is selected from the group consisting of β-alanyl, D-alloisoleucyl D-4-chlorophenylalanyl, D-homophenylalanyl, D-isoleucyl,D-leucyl, D-penicillaminyl, and D-prolyl;

$Xaa_3$ is selected from the group consisting of allothreonyl, aspartyl, glutaminyl, D-glutaminyl, N-methylglutaminyl, glycyl, histidyl, homoseryl, isoleucyl, lysyl(N-epsilon-acetyl), methionyl, seryl, N-methylseryl, threonyl, D-threonyl, tryptyl, tyrosyl, and tyrosyl(O-methyl);

$Xaa_4$ is selected from the group consisting of N-methylalanyl, allothreonyl, glutaminyl, D-glutaminyl, glycyl, homoseryl, leucyl, lysyl(N-epsilon-acetyl), norleucyl, norvalyl, D-norvalyl, N-methylnorvalyl, ornithyl(N-delta-acetyl), 3-(3-pyridyl)alanyl, sarcosyl, seryl, N-methylseryl, threonyl, tryptyl, valyl and N-methylvalyl;

$Xaa_5$ is selected from the group consisting of alanyl, alloisoleucyl, aspartyl, citrullyl, glutaminyl, isoleucyl, D-isoleucyl, N-methylisoleucyl, leucyl, D-leucyl, lysyl, lysyl(N-epsilon-acetyl), D-lysyl(N-epsilon-acetyl), norleucyl, norvalyl, phenylalanyl, prolyl, and D-prolyl;

$Xaa_6$ is selected from the group consisting of arginyl, D-arginyl, citrullyl, histidyl, lysyl, lysyl(N-epsilon-isopropyl), ornithyl, and 3-(3-pyridyl)alanyl;

$Xaa_7$ is absent or selected from the group consisting of N-methyl-D-alanyl, 2-aminobutyryl, 2-aminoisobutyryl, D-glutaminyl, homoprolyl, hydroxyprolyl, leucyl, phenylalanyl, prolyl, D-prolyl, and D-valyl; and $Xaa_8$ is selected from the group consisting of D-alanylamide, azaglycylamide, glycylamide, hydroxyl, D-lysyl(N-epsilon-acetyl)amide, a group represented by the formula $\text{—NH—}(CH_2)_n\text{—CHR}^1R^2$; and a group represented by the formula $\text{—NHR}^3$, wherein n is an integer from 0 to 8; $R^1$ is selected from the group consisting of hydrogen, alkyl, cycloalkenyl, and cycloalkyl; $R^2$ is selected from the group consisting of hydrogen, alkoxy, alkyl, aryl, cycloalkenyl, cycloalkyl, heterocycle, and hydroxyl, provided that when n is 0, $R^2$ is other than alkoxy or hydroxyl; and $R^3$ is selected from the group consisting of hydrogen, cycloalkenyl, cycloalkyl, and hydroxyl.

2. The compound of claim 1 selected from the group consisting of

N-Ac-D-Pro-Thr-Nva-Ile-Arg-ProNHCH$_2$CH$_3$;
N-Ac-D-Leu-Thr-Nva-Ile-Arg-ProNHCH$_2$CH$_3$;
N-Ac-D-Leu-Ser-Nva-Ile-Arg-ProNHCH$_2$CH$_3$;
N-Ac-D-Hphe-Thr-Nva-Ile-Arg-ProNHCH$_2$CH$_3$;
N-Ac-D-4ClPhe-Thr-Nva-Ile-Arg-ProNHCH$_2$CH$_3$;
N-Ac-D-Pen-Thr-Nva-Ile-Arg-ProNHCH$_2$CH$_3$;
N-Ac-bAla-Thr-Nva-Ile-Arg-ProNHCH$_2$CH$_3$ (SEQ ID NO:49);
N-Ac-bAla-Thr-Gln-Ile-Arg-ProNHCH$_2$CH$_3$ (SEQ ID NO:50); and
N-Ac-D-Leu-Asp-Nva-Ile-Arg-ProNHCH$_2$CH$_3$.

3. The compound of claim 1 wherein $Xaa_2$ is D-alloisoleucyl.

4. The compound of claim 3 selected from the group consisting of

N-Ac-D-aIle-Thr-Nva-Ile-Arg-ProNHCH$_2$CH$_3$;
N-Ac-D-aIle-Ser-Ser-Ile-Arg-ProNHCH$_2$CH$_3$;
N-Ac-D-aIle-Thr-Ser-Ile-Arg-ProNHCH$_2$CH$_3$;
N-Ac-D-aIle-Tyr-Nva-Ile-Arg-ProNHCH$_2$CH$_3$;
N-Ac-D-aIle-Ser-Thr-Ile-Arg-ProNHCH$_2$CH$_3$;
N-Ac-D-aIle-Thr-Trp-Ile-Arg-ProNHCH$_2$CH$_3$;
N-Ac-D-aIle-Ser-Ser-Lys(Ac)-Arg-ProNHCH$_2$CH$_3$;
N-Ac-D-aIle-Ser-Ser-Nle-Arg-ProNHCH$_2$CH$_3$;
N-Ac-D-aIle-Ser-Ser-Pro-Arg-ProNHCH$_2$CH$_3$;
N-Ac-D-aIle-Ser-Ser-Nva-Arg-ProNHCH$_2$CH$_3$;
N-Ac-D-aIle-Ser-Ser-Lys-Arg-ProNHCH$_2$CH$_3$;
N-Ac-D-aIle-Ser-Ser-Ile-Arg-ProNHCH(CH$_3$)$_2$;
N-Ac-D-aIle-Ser-Ser-Gln-Arg-ProNHCH$_2$CH$_3$;
N-Ac-D-aIle-Ser-Ser-Cit-Arg-ProNHCH$_2$CH$_3$;
N-Ac-D-aIle-Ser-Ser-Ile-Arg-NHCH$_2$CH$_3$;
N-Ac-D-aIle-Thr-Nva-Ile-Arg-NHCH$_2$CH$_3$; and
N-Ac-D-aIle-Ser-Nva-Lys(Ac)-Arg-NHCH$_2$CH$_3$.

5. The compound of claim 1 wherein $Xaa_2$ is D-isoleucyl.

6. The compound of claim 5 wherein $Xaa_3$ is selected from the group consisting of allothreonyl, aspartyl, glutaminyl, lysyl(N-epsilon-acetyl), methionyl, seryl, and tyrosyl.

7. The compound of claim 6 selected from the group consisting of
N-Ac-D-Ile-alloThr-Nva-Ile-Arg-ProNHCH$_2$CH$_3$;
N-Ac-D-Ile-Ser-Gln-Ile-Arg-ProNHCH$_2$CH$_3$;
N-Ac-D-Ile-Ser-Nva-Ile-Arg-Pro-D-AlaNH$_2$;
N-Ac-D-Ile-Ser-Gln-D-Ile-Arg-ProNHCH$_2$CH$_3$;
N-Ac-D-Ile-Gln-Nva-Ile-Arg-ProNHCH$_2$CH$_3$;
N-Ac-D-Ile-Tyr-Nva-D-Ile-Arg-ProNHCH$_2$CH$_3$;
N-Ac-D-Ile-Met-Nva-Ile-Arg-ProNHCH$_2$CH$_3$;
N-Ac-D-Ile-Asp-Nva-Ile-Arg-ProNHCH$_2$CH$_3$;
N-Ac-D-Ile-alloThr-Nva-Pro-Arg-ProNHCH$_2$CH$_3$;
N-Ac-D-Ile-Met-Gln-Ile-Arg-ProNHCH$_2$CH$_3$; and
N-Ac-D-Ile-Ser-Gln-Ile-Arg-NHCH$_2$CH$_3$.

8. The compound of claim 5 wherein Xaa$_3$ is threonyl.

9. The compound of claim 8 wherein Xaa$_4$ is selected from the group consisting of glutaminyl, D-glutaminyl, norleucyl, N-methylnorvalyl, seryl, and tryptyl.

10. The compound of claim 9 selected from the group consisting of
N-Ac-D-Ile-Thr-Gln-Ile-Arg-ProNHCH$_2$CH$_3$;
N-Ac-D-Ile-Thr-Ser-Ile-Arg-Pro-D-AlaNH$_2$;
N-Ac-D-Ile-Thr-Trp-D-Ile-Arg-ProNHCH$_2$CH$_3$;
N-Ac-D-Ile-Thr-Trp-Ile-Arg-Pro-D-AlaNH$_2$;
N-Ac-D-Ile-Thr-Gln-Ile-Arg-Pro-D-AlaNH$_2$;
N-Ac-D-Ile-Thr-Nle-Ile-Arg-ProNHCH$_2$CH$_3$;
N-Ac-D-Ile-Thr-D-Gln-Ile-Arg-ProNHCH$_2$CH$_3$;
N-Ac-D-Ile-Thr-Gln-Ile-Arg-NHCH$_2$CH$_3$;
N-Ac-D-Ile-Thr-Gln-Lys(Ac)-Arg-NHCH$_2$CH$_3$;
N-Ac-D-Ile-Thr-Ser-Ile-Arg-NHCH$_2$CH$_3$; and
N-Ac-D-Ile-Thr-NMeNva-Ile-Arg-NHCH$_2$CH$_3$.

11. The compound of claim 8 wherein Xaa$_4$ is norvalyl.

12. The compound of claim 11 selected from the group consisting of
N-Ac-D-Ile-Thr-Nva-Ile-Arg-ProNHCH$_2$CH$_3$;
N-Ac-D-Ile-Thr-Nva-Pro-Arg-ProNHCH$_2$CH$_3$;
N-Ac-D-Ile-Thr-Nva-Ile-Arg-D-ProNHCH$_2$CH$_3$;
N-Ac-D-Ile-Thr-Nva-Ile-Arg-Pro-D-AlaNH$_2$;
N-Ac-D-Ile-Thr-Nva-D-Leu-Arg-ProNHCH$_2$CH$_3$;
N-Ac-D-Ile-Thr-Nva-D-Ile-Arg-ProNHCH$_2$CH$_3$;
N-Ac-D-Ile-Thr-Nva-Ile-Arg-Pro-D-Lys(Ac)NH$_2$;
N-Ac-D-Ile-Thr-Nva-D-Lys(Ac)-Arg-ProNHCH$_2$CH$_3$;
N-Ac-D-Ile-Thr-Nva-Lys(Ac)-Arg-ProNHCH$_2$CH$_3$;
N-Ac-D-Ile-Thr-Nva-Ile-His-ProNHCH$_2$CH$_3$;
N-Ac-D-Ile-Thr-Nva-Ile-3-Pal-ProNHCH$_2$CH$_3$;
N-Ac-D-Ile-Thr-Nva-Ile-D-Arg-ProNHCH$_2$CH$_3$;
N-Ac-D-Ile-Thr-Nva-Ile-ArgNHCH$_2$CH$_3$; and
N-Ac-D-Ile-Thr-Nva-Lys(Ac)-Arg-NHCH$_2$CH$_3$.

* * * * *